(12) United States Patent
Roberson et al.

(10) Patent No.: US 11,883,057 B2
(45) Date of Patent: *Jan. 30, 2024

(54) ULTRASONIC SURGICAL INSTRUMENT WITH TRANSDUCER SLIP JOINT

(71) Applicants: Cilag GmbH International, Zug (CH); SAMTEC INC., New Albany, IN (US)

(72) Inventors: Eric Roberson, Cincinnati, OH (US); James E. Borgelt, New Albany, IN (US); Douglas E. McCartin, New Albany, IN (US)

(73) Assignees: Cilag GmbH International, Zug (CH); SAMTEC Inc., New Albany, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/575,219

(22) Filed: Jan. 13, 2022

(65) Prior Publication Data

US 2022/0192695 A1 Jun. 23, 2022

Related U.S. Application Data

(63) Continuation of application No. 16/919,290, filed on Jul. 2, 2020, now Pat. No. 11,350,961, which is a
(Continued)

(51) Int. Cl.
*A61B 17/32* (2006.01)
*A61N 7/02* (2006.01)
(Continued)

(52) U.S. Cl.
CPC ............. *A61B 17/320068* (2013.01); *A61B 17/320092* (2013.01); *A61B 90/03* (2016.02);
(Continued)

(58) Field of Classification Search
CPC .... A61B 17/320068; A61B 17/320092; A61B 90/03; A61B 2017/00477;
(Continued)

(56) References Cited

U.S. PATENT DOCUMENTS 4,170,234 A 10/1979 Graham
5,322,055 A 6/1994 Davison et al.
(Continued)

FOREIGN PATENT DOCUMENTS

CN 105125255 A 12/2015
JP H09-299381 A 11/1997
(Continued)

OTHER PUBLICATIONS

Chinese Office Action, The First Office Action, and First Search, dated Feb. 11, 2022 for Application No. CN 201780077220.6, 10 pgs.
(Continued)

*Primary Examiner* — Truc T Nguyen
(74) *Attorney, Agent, or Firm* — Frost Brown Todd LLP

(57) ABSTRACT

A surgical instrument for use during a surgical procedure includes an instrument body, an ultrasonic transducer assembly extending along a longitudinal axis, a power cord, and a transducer slip joint. The ultrasonic transducer assembly is rotatably mounted within the instrument body about the longitudinal axis and defines a first outer profile. The power cord projects from the instrument body to provide electrical power to the ultrasonic transducer assembly for operating an acoustic waveguide. The transducer slip joint is positioned between the power cord and the ultrasonic transducer assembly and electrically and mechanically connects the power cord to the ultrasonic transducer assembly. The ultrasonic transducer assembly selectively rotates relative to the power cord for inhibiting the power cord from winding upon rotation of the ultrasonic transducer assembly. The transducer slip joint also defines a second outer profile that fits within the first outer profile of the ultrasonic transducer assembly.

20 Claims, 10 Drawing Sheets

Related U.S. Application Data continuation of application No. 16/276,708, filed on Feb. 15, 2019, now Pat. No. 10,751,079, which is a continuation of application No. 15/795,851, filed on Oct. 27, 2017, now Pat. No. 10,363,058, which is a continuation of application No. 15/378,488, filed on Dec. 14, 2016, now Pat. No. 9,833,256.

(51) Int. Cl.
    *A61B 90/00*     (2016.01)
    *A61B 17/00*     (2006.01)
    *A61B 18/00*     (2006.01)

(52) U.S. Cl.
    CPC ...... *A61N 7/02* (2013.01); *A61B 2017/00477* (2013.01); *A61B 2017/320071* (2017.08); *A61B 2017/320094* (2017.08); *A61B 2017/320095* (2017.08); *A61B 2018/0063* (2013.01); *A61B 2018/00345* (2013.01); *A61B 2018/00601* (2013.01); *A61B 2018/00619* (2013.01); *A61B 2090/031* (2016.02)

(58) Field of Classification Search
CPC ....... A61B 2017/320071; A61B 2017/320094; A61B 2017/320095; A61B 2018/00345; A61B 2018/00601; A61B 2018/00619; A61B 2018/0063; A61B 2090/031; A61B 17/00234; A61B 17/29; A61B 18/04; A61B 2017/320069; A61N 7/02
See application file for complete search history.

(56) References Cited

U.S. PATENT DOCUMENTS

| | | | |
|---|---|---|---|
| 5,873,873 A | 2/1999 | Smith et al. | |
| 5,897,523 A | 4/1999 | Wright et al. | |
| 5,980,510 A | 11/1999 | Tsonton et al. | |
| 5,989,264 A | 11/1999 | Wright | |
| 6,063,098 A | 5/2000 | Houser et al. | |
| 6,090,120 A | 7/2000 | Wright et al. | |
| 6,099,537 A | 8/2000 | Sugai et al. | |
| 6,204,592 B1 * | 3/2001 | Hur | A61C 1/07 310/323.12 |
| 6,325,811 B1 | 12/2001 | Messerly | |
| 6,454,782 B1 | 9/2002 | Schwemberger | |
| 6,589,200 B1 | 7/2003 | Schwemberger et al. | |
| 6,752,815 B2 | 6/2004 | Beaupre | |
| 6,773,444 B2 | 8/2004 | Messerly | |
| 6,783,524 B2 | 8/2004 | Anderson et al. | |
| 7,135,030 B2 | 11/2006 | Schwemberger et al. | |
| 7,621,930 B2 | 11/2009 | Houser | |
| 8,461,744 B2 | 6/2013 | Wiener et al. | |
| 8,591,536 B2 | 11/2013 | Robertson | |
| 8,623,027 B2 | 1/2014 | Price et al. | |
| 8,734,476 B2 | 5/2014 | Rhee et al. | |
| 8,951,248 B2 | 2/2015 | Messerly et al. | |
| 8,986,302 B2 | 3/2015 | Aldridge et al. | |
| 9,023,071 B2 | 5/2015 | Miller et al. | |
| 9,095,367 B2 | 8/2015 | Olson et al. | |
| 9,381,058 B2 | 7/2016 | Houser et al. | |
| 9,393,037 B2 | 7/2016 | Olson et al. | |
| 9,402,682 B2 | 8/2016 | Worrell et al. | |
| 9,408,622 B2 | 8/2016 | Stulen et al. | |
| 9,629,652 B2 | 4/2017 | Mumaw et al. | |
| 9,833,256 B1 | 12/2017 | Roberson et al. | |
| 10,363,058 B2 | 7/2019 | Roberson et al. | |
| 10,751,079 B2 | 8/2020 | Roberson et al. | |
| 2002/0177373 A1 | 11/2002 | Shibata et al. | |
| 2006/0079874 A1 | 4/2006 | Faller et al. | |
| 2007/0191713 A1 | 8/2007 | Eichmann et al. | |
| 2007/0276352 A1 | 11/2007 | Crocker et al. | |
| 2007/0282333 A1 | 12/2007 | Fortson et al. | |
| 2008/0200940 A1 | 8/2008 | Eichmann et al. | |
| 2009/0090763 A1 | 4/2009 | Zemlok et al. | |
| 2011/0017801 A1 | 1/2011 | Zemlok et al. | |
| 2011/0028898 A1 | 2/2011 | Clark, III et al. | |
| 2011/0139851 A1 | 6/2011 | McCuen | |
| 2011/0196286 A1 | 8/2011 | Robertson et al. | |
| 2011/0204119 A1 | 8/2011 | McCuen | |
| 2012/0116261 A1 | 5/2012 | Mumaw et al. | |
| 2012/0116265 A1 | 5/2012 | Houser et al. | |
| 2012/0116390 A1 | 5/2012 | Madan | |
| 2012/0292367 A1 | 11/2012 | Morgan et al. | |
| 2013/0090675 A1 | 4/2013 | Mumaw et al. | |
| 2013/0096468 A1 | 4/2013 | Rhee et al. | |
| 2013/0244453 A1 | 9/2013 | Sakamoto | |
| 2013/0289565 A1 | 10/2013 | Hassler, Jr. et al. | |
| 2014/0135804 A1 | 5/2014 | Weisenburgh, II et al. | |
| 2014/0235085 A1 | 8/2014 | Su et al. | |
| 2014/0246471 A1 | 9/2014 | Jaworek et al. | |
| 2014/0246473 A1 | 9/2014 | Auld | |
| 2014/0246476 A1 | 9/2014 | Hall et al. | |
| 2014/0249557 A1 | 9/2014 | Koch, Jr. et al. | |
| 2014/0276055 A1 | 9/2014 | Barthe et al. | |
| 2014/0276761 A1 | 9/2014 | Parihar et al. | |
| 2015/0004837 A1 | 1/2015 | Brichard et al. | |
| 2015/0080924 A1 | 3/2015 | Stulen et al. | |
| 2015/0157354 A1 | 6/2015 | Bales, Jr. et al. | |
| 2015/0209035 A1 | 7/2015 | Zemlok | |
| 2015/0280384 A1 | 10/2015 | Leimbach et al. | |
| 2015/0305735 A1 | 10/2015 | Gorek et al. | |
| 2015/0335347 A1 | 11/2015 | Hirai et al. | |
| 2016/0066911 A1 | 3/2016 | Baber et al. | |
| 2016/0066915 A1 | 3/2016 | Baber et al. | |
| 2016/0121143 A1 | 5/2016 | Mumaw et al. | |
| 2016/0270780 A1 | 9/2016 | Hall et al. | |
| 2016/0302817 A1 | 10/2016 | Worrell et al. | |
| 2017/0042508 A1 * | 2/2017 | Havel | A61B 8/12 |
| 2018/0161057 A1 | 6/2018 | Roberson et al. | |
| 2018/0161059 A1 | 6/2018 | Lesko et al. | |
| 2018/0161060 A1 | 6/2018 | Roberson et al. | |
| 2019/0099180 A1 | 4/2019 | Leimbach et al. | |
| 2020/0093487 A1 | 3/2020 | Baber et al. | |
| 2022/0240970 A1 * | 8/2022 | Cowley | A61B 17/320068 |

FOREIGN PATENT DOCUMENTS

| | | |
|---|---|---|
| JP | H10-127655 A | 5/1998 |
| JP | 2011-189177 A | 9/2011 |

OTHER PUBLICATIONS

European Examination Report, dated Jun. 29, 2022 for Application No. EP 17817555.0, 7 pgs.

Indian Office Action, Examination Report, dated Dec. 8, 2021 for Application No. IN 201917021039, 6 pgs.

International Search Report and Written Opinion dated Feb. 13, 2018, for International Application No. PCT/US2017/063869, 10 pages.

Japanese Office Action, Notification of Reasons for Refusal, and Search Report by Registered Search Organization, dated Oct. 21, 2021 for Application No. JP 2019-531711, 19 pgs.

Korean Office Action, Written Decision on Registration, dated May 25, 2023 for Application No. KR 2019-7020373, 4 pgs.

U.S. Appl. No. 14/258,179, entitled "Ultrasonic Surgical Device with Articulating End Effector," filed Apr. 22, 2014.

U.S. Appl. No. 61/410,603, entitled "Energy-Based Surgical Instruments," filed Nov. 5, 2010.

* cited by examiner

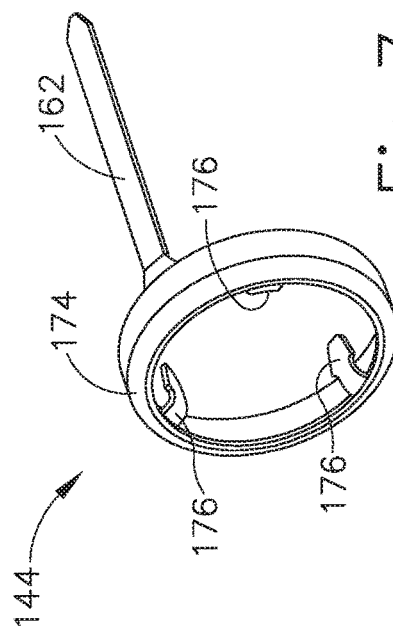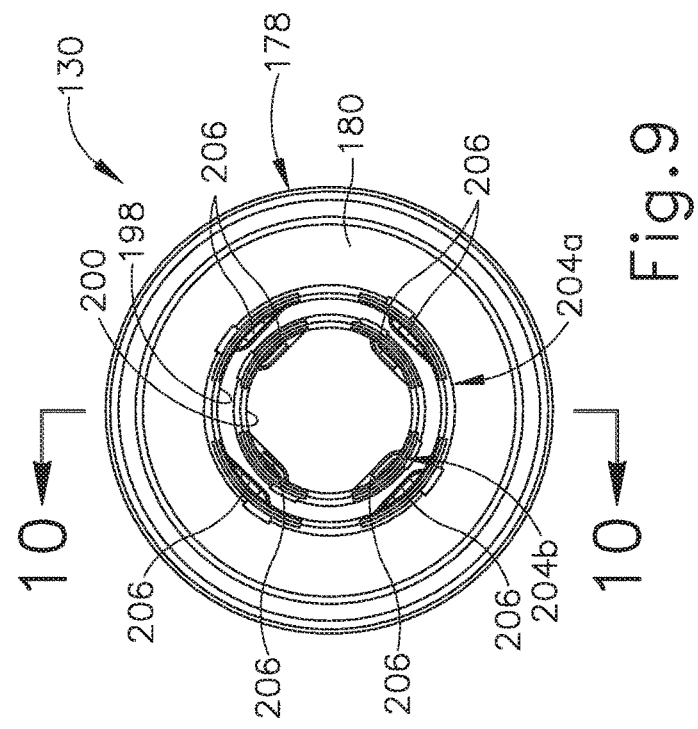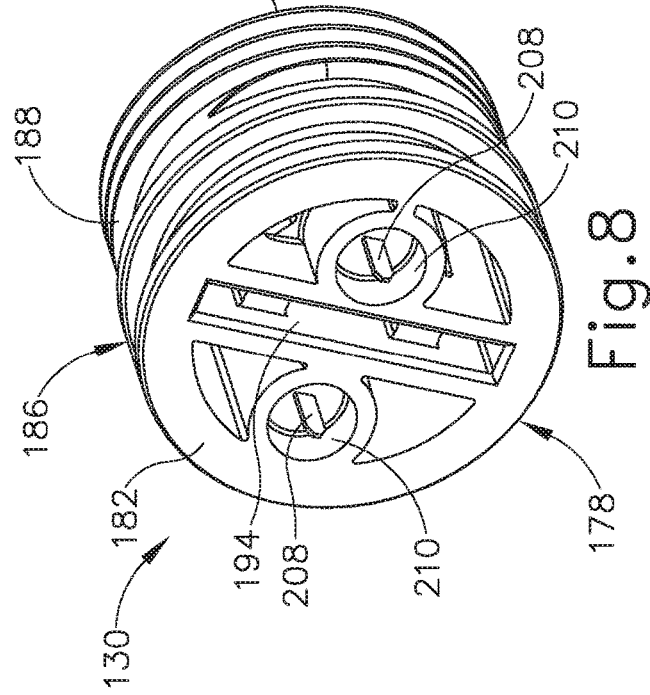

ULTRASONIC SURGICAL INSTRUMENT WITH TRANSDUCER SLIP JOINT

This application is a continuation of U.S. patent application Ser. No. 16/919,290, filed Jul. 2, 2020, issued as U.S. Pat. No. 11,350,961 on Jun. 7, 2022, entitled "Ultrasonic Surgical Instrument with Transducer Slip Joint," which is a continuation of U.S. patent application Ser. No. 16/276,708, filed Feb. 15, 2019, entitled "Ultrasonic Surgical Instrument with Transducer Slip Joint," now U.S. Pat. No. 10,751,079, issued on Aug. 25, 2020, which is a continuation of U.S. patent application Ser. No. 15/795,851, filed Oct. 27, 2017, entitled "Ultrasonic Surgical Instrument with Transducer Slip Joint," now U.S. Pat. No. 10,363,058, issued on Jul. 30, 2019, which is a continuation of U.S. patent application Ser. No. 15/378,488, filed Dec. 14, 2016, entitled "Ultrasonic Surgical Instrument with Transducer Slip Joint," now U.S. Pat. No. 9,833,256, issued on Dec. 5, 2017.

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; and U.S. Pub. No. 2010/0069940, entitled "Ultrasonic Device for Fingertip Control," published Mar. 18, 2010, now U.S. Pat. No. 9,023,071, issued on May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, now U.S. Pat. No. 9,381,058, issued on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section and/or a bendable ultrasonic waveguide. Examples of such ultrasonic surgical instruments are disclosed in U.S. Pat. No. 5,897,523, entitled "Articulating Ultrasonic Surgical Instrument," issued Apr. 27, 1999, the disclosure of which is incorporated by reference herein; U.S. Pat. No. 5,989,264, entitled "Ultrasonic Polyp Snare," issued Nov. 23, 1999, the disclosure of which is incorporated by reference herein; U.S. Pat. No. 6,063,098, entitled "Articulable Ultrasonic Surgical Apparatus," issued May 16, 2000, the disclosure of which is incorporated by reference herein; U.S. Pat. No. 6,090,120, entitled "Articulating Ultrasonic Surgical Instrument," issued Jul. 18, 2000, the disclosure of which is incorporated by reference herein; U.S. Pat. No. 6,454,782, entitled "Actuation Mechanism for Surgical Instruments," issued Sep. 24, 2002, the disclosure of which is incorporated by reference herein; U.S. Pat. No. 6,589,200, entitled "Articulating Ultrasonic Surgical Shears," issued Jul. 8, 2003, the disclosure of which is incorporated by reference herein; U.S. Pat. No. 6,752,815, entitled "Method and Waveguides for Changing the Direction of Longitudinal Vibrations," issued Jun. 22, 2004, the disclosure of which is incorporated by reference herein; U.S. Pat. No. 7,135,030, entitled "Articulating Ultrasonic Surgical Shears," issued Nov. 14, 2006; U.S. Pat. No. 7,621,930, entitled "Ultrasound Medical Instrument Having a Medical Ultrasonic Blade," issued Nov. 24, 2009, the disclosure of which is incorporated by reference herein; U.S. Pub. No. 2014/0005701, published Jan. 2, 2014, now U.S. Pat. No. 9,393,037, issued on Jul. 19, 2016, entitled "Surgical Instruments with Articulating Shafts," the disclosure of which is incorporated by reference herein; U.S. Pub. No. 2014/0005703, entitled "Surgical Instruments with Articulating Shafts," published Jan. 2, 2014, now U.S. Pat. No. 9,408,622, issued on Aug. 9, 2016, the disclosure of which is incorporated by reference herein; U.S. Pub. No.

2014/0114334, entitled "Flexible Harmonic Waveguides/ Blades for Surgical Instruments," published Apr. 24, 2014, now U.S. Pat. No. 9,095,367, issued on Aug. 4, 2015, the disclosure of which is incorporated by reference herein; U.S. Pub. No. 2015/0080924, entitled "Articulation Features for Ultrasonic Surgical Instrument," published Mar. 19, 2015, now U.S. Pat. No. 10,172,636, issued Jan. 8, 2019, the disclosure of which is incorporated by reference herein; and U.S. patent application Ser. No. 14/258,179, entitled "Ultrasonic Surgical Device with Articulating End Effector," filed Apr. 22, 2014, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 7 depicts a front perspective view of an electrical contact of the static coupling of FIG. 5;

FIG. 8 depicts a front perspective view of a dynamic coupling of the transducer slip joint of FIG. 4;

FIG. 9 depicts a rear elevational view of the dynamic coupling of FIG. 8;

Figure 1:
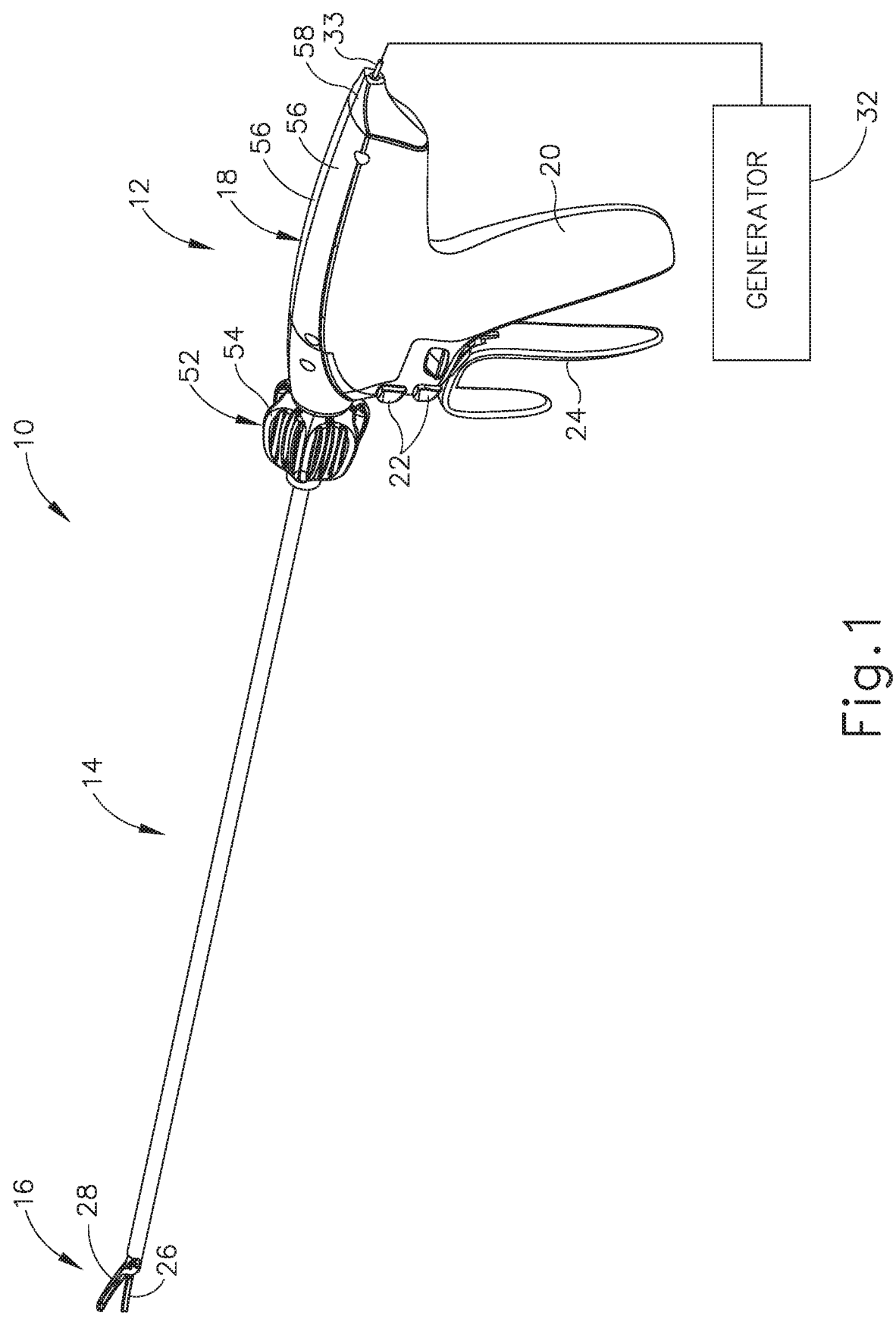
FIG. 1 depicts a perspective view of an ultrasonic surgical instrument having a handle assembly, a shaft assembly, and an end effector.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. The terms "proximal" and "distal" are thus relative terms and not intended to unnecessarily limit the invention described herein.

I. Exemplary Ultrasonic Surgical Instrument

FIG. 1 shows an exemplary ultrasonic surgical instrument (10). At least part of instrument (10) may be constructed and operable in accordance with at least some of the teachings of any of the various patents, patent application publications, and patent applications that are cited herein. As described therein and as will be described in greater detail below, instrument (10) is operable to cut tissue and seal or weld tissue (e.g., a blood vessel, etc.) substantially simultaneously.

Instrument (10) of the present example comprises a handle assembly (12), a shaft assembly (14), and an end effector (16). Handle assembly (12) comprises a body (18) including a pistol grip (20) and a pair of buttons (22). Handle assembly (12) also includes a trigger (24) that is pivotable toward and away from pistol grip (20). It should be understood, however, that various other suitable configurations may be used, including but not limited to a scissor grip configuration. End effector (16) includes an ultrasonic blade (26) and a pivoting clamp arm (28). Clamp arm (28) is coupled with trigger (24) such that clamp arm (28) is pivotable toward ultrasonic blade (26) in response to pivoting of trigger (24) toward pistol grip (20); and such that clamp arm (28) is pivotable away from ultrasonic blade (26) in response to pivoting of trigger (24) away from pistol grip (20). Various suitable ways in which clamp arm (28) may be coupled with trigger (24) will be apparent to those of ordinary skill in the art in view of the teachings herein. In some versions, one or more resilient members are used to bias clamp arm (28) and/or trigger (24) to the open position shown in FIG. 1.

Figure 3:
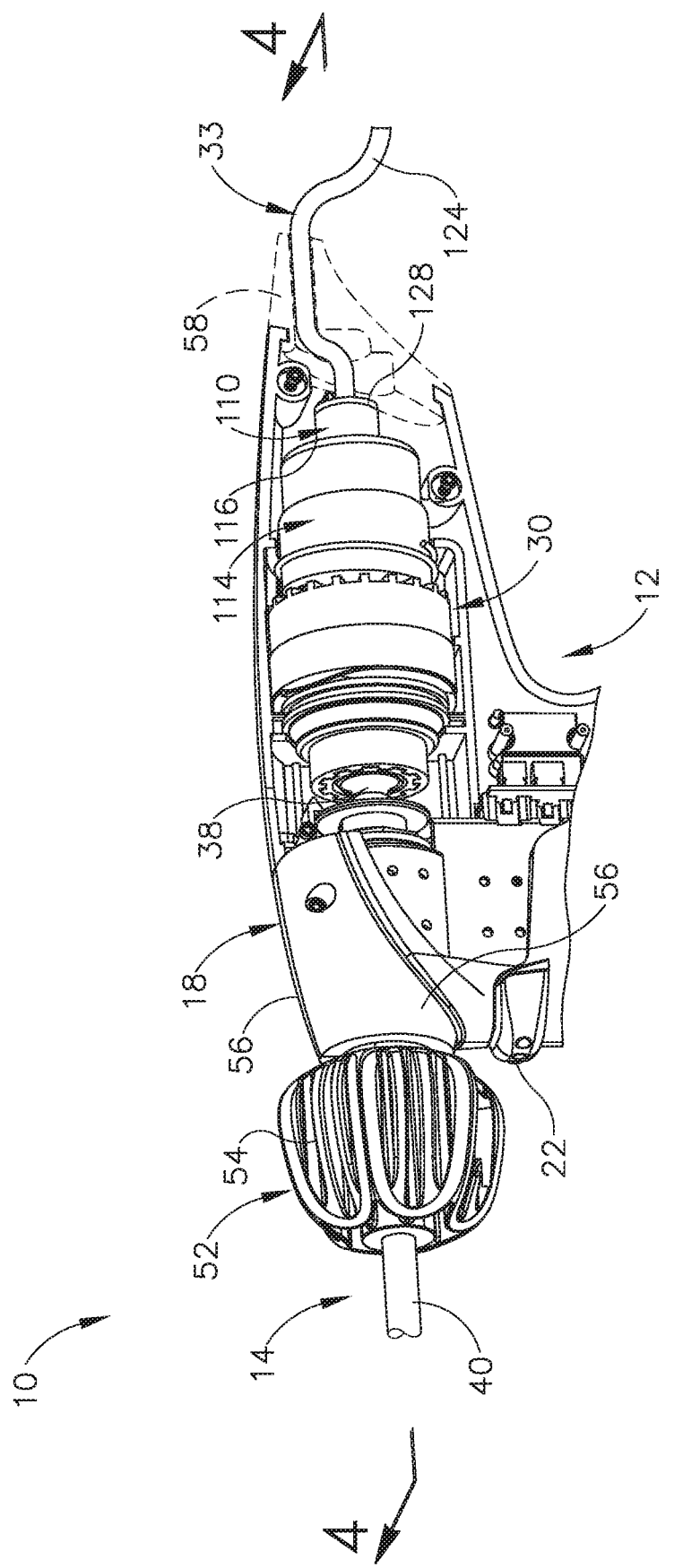
FIG. 3 depicts an enlarged perspective view of a handle assembly of the ultrasonic surgical instrument of FIG. 1 having various components removed for improved visibility of a first exemplary transducer slip joint.
Figure 4:
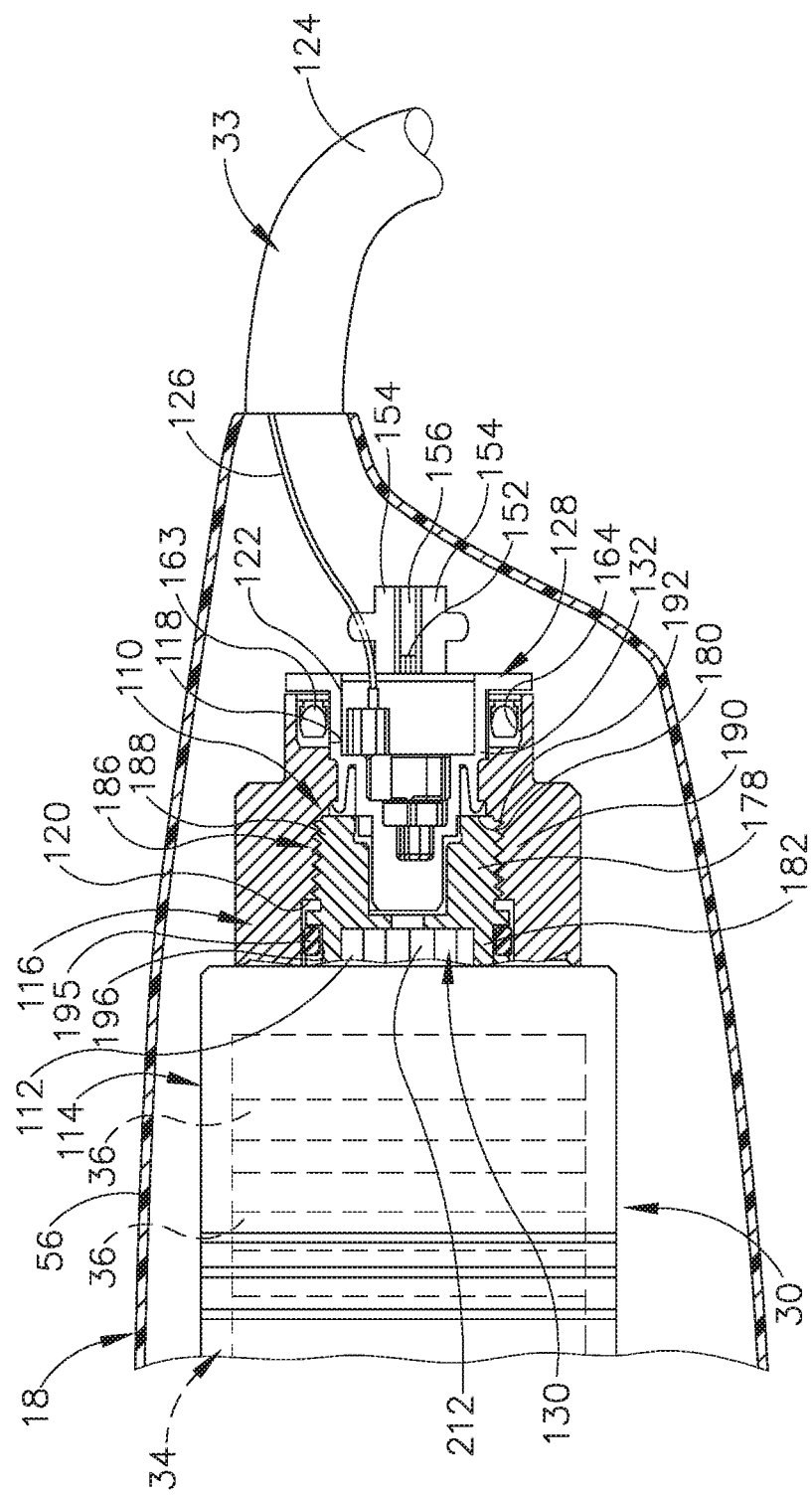
FIG. 4 depicts an enlarged cross-sectional view of the handle assembly with the transducer slip joint of FIG. 3 taken along section line 4-4 of FIG. 3.

As best seen in FIGS. 3 and 4, an ultrasonic transducer assembly (30) is positioned within body (18) of handle assembly (12). Transducer assembly (30) is coupled with a generator (32) via a power cord (33), such that transducer assembly (30) receives electrical power from generator (32). Power cord (33) may also be referred to as cable (33) as described herein. Transducer assembly (30) includes a transducer housing (114) that contains an ultrasonic transducer (34) having a plurality of piezoelectric elements (36). Piezoelectric elements (36) in transducer assembly (30) convert electrical power from generator (32) into ultrasonic vibrations. Generator (32) may include a power source and control module that is configured to provide a power profile to transducer assembly (30) that is particularly suited for the generation of ultrasonic vibrations through transducer assembly (30). By way of example only, generator (32) may comprise a GEN04 or GEN11 sold by Ethicon Endo-Surgery, Inc. of Cincinnati, Ohio. In addition, or in the alternative, generator (32) may be constructed in accordance with at least some of the teachings of U.S. Pub. No. 2011/0087212, entitled "Surgical Generator for Ultrasonic and Electrosurgical Devices," published Apr. 14, 2011, now U.S. Pat. No. 8,986,302, issued on Mar. 24, 2015, the disclosure of which is incorporated by reference herein. It should also be understood that at least some of the functionality of generator (32) may be integrated into handle assembly (12), and that handle assembly (12) may even include a battery or other on-board power source such that cable (14) is omitted, while other cables may alternatively be used for electrically coupling various components. Still other suitable forms that generator (32) may take, as well as various features and operabilities that generator (32) may provide, will be apparent to those of ordinary skill in the art in view of the teachings herein.

A. Exemplary End Effector and Shaft Assembly

Figure 2:
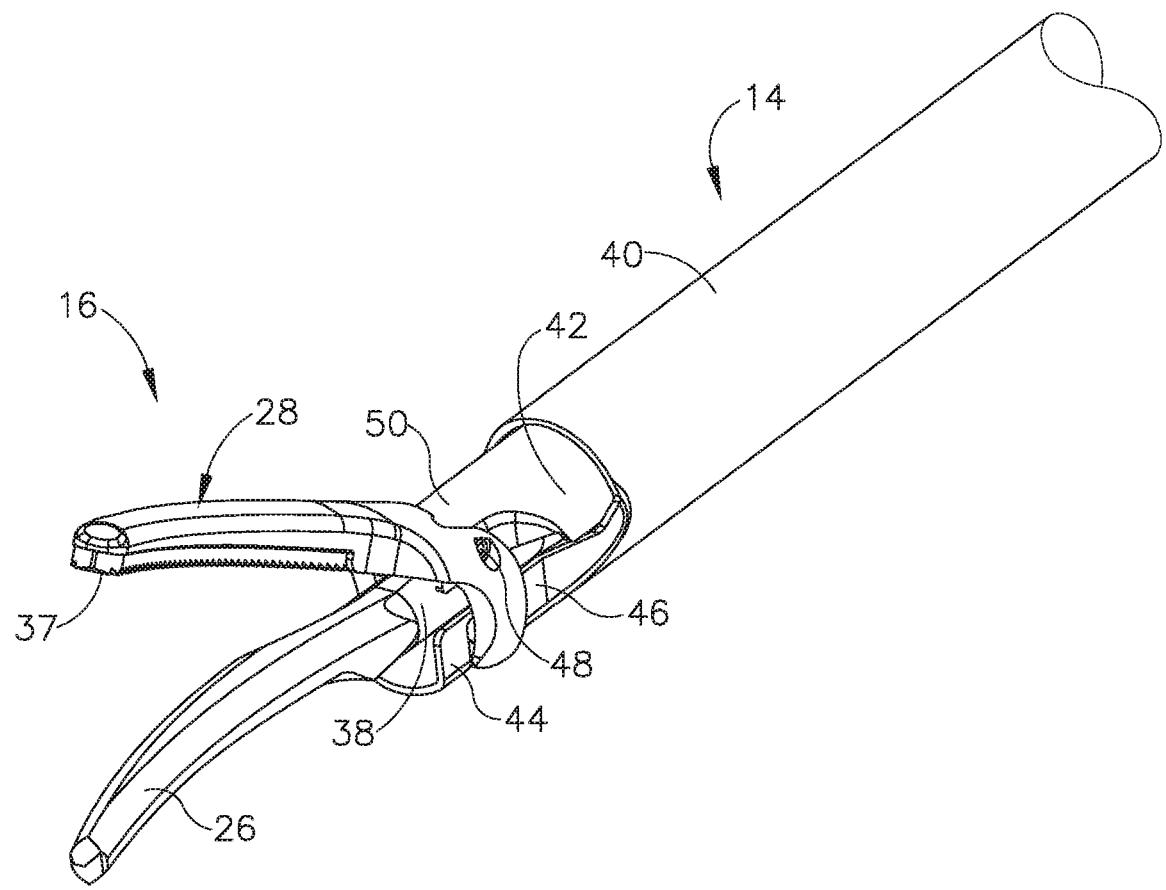
FIG. 2 depicts a perspective view of the end effector of FIG. 1.

As best seen in FIGS. 1-2, end effector (16) of this example comprises a clamp arm (28) and ultrasonic blade (28) as discussed briefly above. Clamp arm (28) includes a clamp pad (37), which faces blade (26). Clamp arm (28) is pivotable toward and away from blade (26) to selectively compress tissue between clamp pad (37) and blade (26). More particularly, blade (26) is an integral feature of a distal end of an acoustic waveguide (38), which extends coaxially through tubes (40, 42), and which is configured to communicate ultrasonic vibrations to blade (26) as will be described in greater detail below.

Shaft assembly (14) comprises an outer tube (40) and an inner tube (42). Outer tube (40) is operable to translate longitudinally relative to inner tube (42) to selectively pivot clamp arm (28) toward and away from blade (26). To accomplish this, and as best seen in FIG. 2, integral pin features (not shown) extending inwardly from respective projections (44) of clamp arm (28) pivotally secure a first portion of clamp arm (28) to a distally projecting tongue (46) of outer tube (40); while an inserted pin (48) pivotally secures a second portion of clamp arm (28) to a distally projecting tongue (50) of inner tube (42). Thus, tubes (40, 42) cooperate to pivot clamp arm (28) toward blade (26) when outer tube (40) is retracted proximally relative to inner tube (42). It should be understood that clamp arm (28) may be pivoted back away from blade (26) by translating outer tube (40) distally relative to inner tube (42). In an exemplary use, clamp arm (28) may be pivoted toward blade (26) to grasp, compress, seal, and sever tissue captured between clamp pad (37) and blade (26). Clamp arm (28) may be pivoted away from blade (26) to release tissue from between clamp pad (37) and blade (26); and/or to perform blunt dissection of tissue engaging opposing outer surfaces of clamp arm (28) and blade (26). In some alternative versions, inner tube (42) translates while outer tube (40) remains stationary to provide pivotal movement of clamp arm (28).

As shown in FIGS. 1-2, shaft assembly (14) of the present example extends distally from handle assembly (12). A rotation control assembly (52) has rotation control member in the form of rotation control knob (54), which is secured to a proximal portion of outer tube (40). Knob (54) is rotatable relative to body (18), such that shaft assembly (14) is rotatable about the longitudinal axis defined by outer tube (40), relative to handle assembly (12). Such rotation may provide rotation of end effector (16) and shaft assembly (30) unitarily, which also includes unitary rotation of acoustic waveguide (38) coupled with transducer assembly (30) within handle assembly (12). In alternative embodiment, various rotatable features may simply be omitted and/or replaced with alternative rotatable features, if desired. While the present shaft assembly (14) is generally rigid and linear, it will be appreciated that alternative shaft assemblies may include an articulation section (not shown) for deflecting end effector (16) at various lateral deflection angles relative to a longitudinal axis defined by outer tube (40). It will be appreciated that articulation section (not shown) may take a variety of forms. By way of example only, articulation section (now shown) may be configured in accordance with one or more teachings of U.S. Pub. No. 2012/0078247, now U.S. Pat. No. 9,402,682, issued on Aug. 2, 2016, the disclosure of which is incorporated by reference herein. As another merely illustrative example, articulation section (not shown) may be configured in accordance with one or more teachings of U.S. Pub. No. 2014/0005701, now U.S. Pat. No. 9,393,037, and/or U.S. Pub. No. 2014/0114334, now U.S. Pat. No. 9,095,367, issued on Aug. 4, 2015, the disclosures of which are incorporated by reference herein. Various other suitable forms that articulation section (not shown) may take will be apparent to those of ordinary skill in the art in view of the teachings herein.

Furthermore, in the present example, shaft assembly (14) and end effector (16) extending distally therefrom are replaceable components. Shaft assembly (14) may thus be detached from handle assembly (12) after use for disposal and replaced with another assembly, such as another shaft assembly (14) and end effector (16), for further use. Alternatively, shaft assembly (14) may be integrally connected with handle assembly (12) such that the entirety of surgical instrument (10) may be reusable or simply disposable after a predetermined number of uses. In any case the invention described herein is not intended to be limited to use with only replaceable or reusable components as described herein.

B. Exemplary Handle Assembly

As seen in FIGS. 1 and 3, handle assembly (12) is reusable as discussed above and comprises body (18) defined by a pair of complementary housings (56) joined together. Housings (56) collectively define pistol grip (20) and includes a cord support base (58) through which cable (33) extends between transducer assembly (30) and generator (32). While body (18) includes pistol grip (20) in this example, it should be understood that any other suitable kind of grip may be used.

Waveguide (38) extends proximally through knob (54) and into body (18) to mechanically couple with transducer assembly (30). When waveguide (38) is sufficiently coupled with transducer assembly (30), ultrasonic vibrations that are generated by transducer assembly (30) are communicated along waveguide (38) to reach blade (26). In the present example, the distal end of blade (26) is located at a position corresponding to an anti-node associated with resonant ultrasonic vibrations communicated through waveguide (38), in order to tune the acoustic assembly to a preferred resonant frequency $f_o$ when the acoustic assembly is not loaded by tissue. When transducer assembly (30) is energized, the distal end of blade (26) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (30) of the present example is activated, these mechanical oscillations are transmitted through waveguide (38) to reach blade (26), thereby providing oscillation of blade (26) at the resonant ultrasonic frequency. Thus, when tissue is secured between blade (26) and clamp pad (37), the ultrasonic oscillation of blade (26) may simultaneously sever the tissue and denature the proteins in adjacent tissue cells, thereby providing a coagulative effect with relatively little thermal spread. In some versions, an electrical current may also be provided through blade (26) and/or clamp pad (37) to also seal the tissue.

Further exemplary features and operabilities for disposable and/or reusable portions of surgical instrument (10) will be described in greater detail below, while other variations will be apparent to those of ordinary skill in the art in view of the teachings.

II. Transducer Assembly Rotation and Reduced Cord Wind

As described above with respect to surgical instrument (10), selective rotation of knob (54) collectively rotates the remainder of shaft assembly (14), end effector (16), waveguide (38), and transducer assembly (30) relative to handle assembly (12). In turn, cable (33), which is electrically and mechanically coupled with transducer assembly (30), may similarly rotate in various examples to accommodate rotation of transducer assembly (30). However, cable (33) may be rigidly connected to generator (32), body (18) of handle assembly (12), or any other component, which may cause the cable (33) to wind between the rotatable transducer assembly (30) and such a rigid, non-rotatable connection. Such cable wind may generate a reactionary torque within cable (33) that reduces a user's ability to selectively rotate end effector (16) via knob (54) during use. Moreover, continuous cable wind may further deteriorate the structural integrity of cable (33), resulting in decreased performance and even permanent damage to surgical instrument (10).

It may thus be desirable to provide a rotatable slip coupling between transducer assembly (30) and cable (33) such that transducer assembly (30) is configured to rotate relative to cable (33) to reduce the likelihood of cable wind. Various alternative connectors for providing a rotatable slip coupling are described in U.S. Pat. Pub. No. 2012/0116261, now abandoned, and U.S. Pat. Pub. No. 2013/0090675, now U.S. Pat. No. 9,629,652, issued on Apr. 25, 2017, the disclosures of which are incorporated by reference herein. While these various alternative connectors may be desirable in some instances, it will be appreciated that such alternative connectors may not be as desirable for one or more reasons depending on the particulars of the surgical instrument. The following description thus relates to a first exemplary slip joint (110) and a second exemplary slip joint (310) for use with surgical instrument (10) discussed above in greater detail. Each of slip joints (110, 310) is configured to electrically and mechanically connect cable (33) to transducer assembly (30) relative to the cable (33) for inhibiting cable (33) from winding upon rotation of transducer assembly (30). Accordingly, like numbers described herein indicate like features with respect to each exemplary slip joint (110, 310). It should be understood that each slip joint (110, 310) is configured to enable free rotation of transducer assembly (30) relative to cable (33) while providing continuous electrical continuity between transducer assembly (30) and cable (33).

A. First Exemplary Slip Joint

FIGS. 3-4 show a first exemplary slip joint (110) connected with transducer assembly (30) having a transducer (112) contained within transducer housing (114), which may also be referred to as a transducer can. Slip joint (110) is integrated into a distal portion (116) of transducer housing (114) having a proximal hollow (118) and an adjacent distal hollow (120). Proximal hollow (118) extends between distal hollow (120) and a proximal opening (122) to the exterior of transducer housing (114) within body (18). In the present example, slip joint (110) is positioned generally within distal hollow (120) and proximal hollow (122) along the longitudinal axis. More particularly, slip joint (110), distal hollow (120), and proximal hollow (122) are concentrically aligned along the longitudinal axis, and distal hollow (120) has a larger diameter than proximal hollow (122).

Transducer housing (114) defines an outer profile about the longitudinal axis in a plane that is transverse to the longitudinal axis. Slip joint (110) is integrated into distal portion (116) of transducer housing (114) such that slip joint (110) is transversely sized to fit within the outer profile of transducer housing (114). In the present example, an outer profile in the transverse plane of slip joint (110) is smaller than the outer profile of transducer housing (114) about the longitudinal axis. In addition, transducer (34) with piezoelectric elements (36) also defines an outer profile in the transverse plane that is smaller than the outer profile of transducer housing (114). By way of further example, the outer profile of the transducer (34) with piezoelectric elements (36) is larger than the outer profile of slip joint (110).

As used herein, the phrase "fit within" with respect to outer profiles also includes one or more outer profiles overlapping with another outer profile in addition to smaller outer profiles that "fit within." For example, an exemplary outer profile of another slip joint may be the same as an exemplary outer profile of another transducer housing and still be considered to "fit within" the outer profile of the transducer housing. The invention is thus not intended to be unnecessarily limited to one outer profile being smaller than an another other profile to fit therein and may include one outer profile that overlaps with another outer profile.

Cable (33) rigidly connects to body (18) at cord support base (58), which is configured to support cable (33) in use and reduce stress concentrations from accumulating in the cable (33) at the connection with body (18). Cable (33) generally includes an outer cover (124) that shields at least a pair of wires (126). In some versions, wires (126) are respectively positive and negative wires (126) that extend from generator (32) (see FIG. 1) for delivering electrical power therealong to transducer assembly (30) via slip joint (110). It should be understood that various other kinds of wires may also be contained in cable (33), including but not limited to wires that provide communication of data in addition to or in lieu of providing communication of operating power.

To this end, slip joint (110) includes a proximal coupling (128) positioned in proximal hollow (118) and a distal coupling (130) positioned within distal hollow (120). Proximal and distal couplings (128, 130) are more particularly static and dynamic couplings (128, 130), respectively, as each relates to body (18). In other words, static coupling (128) is rotationally fixed about the longitudinal axis relative to body (18), whereas dynamic coupling (130) is fixed with rotatable transducer housing (114) to rotate about the longitudinal axis relative to body (18). While static coupling (128) is generally fixed so as not to rotate relative to body (18) or cable (33), alterative proximal couplings may rotate or otherwise move to some extent so long as these alternative proximal couplings are limited in movement, thereby inhibiting cable (33) from overly winding to either decrease performance and/or damage cable (33). Proximal coupling (128) is thus not intended to be unnecessarily limited to one fixed position in accordance with the invention described herein. In any case, static coupling (128) receives electrical operating power from positive and negative wires (126) and directs electrical power to dynamic coupling (130) for powering transducer assembly (30). Transducer housing (114) in turn mechanically supports static and dynamic couplings (128, 130) against each other to transmit the electrical power therebetween while providing for relative motion between static and dynamic couplings (128, 130).

Figure 5:
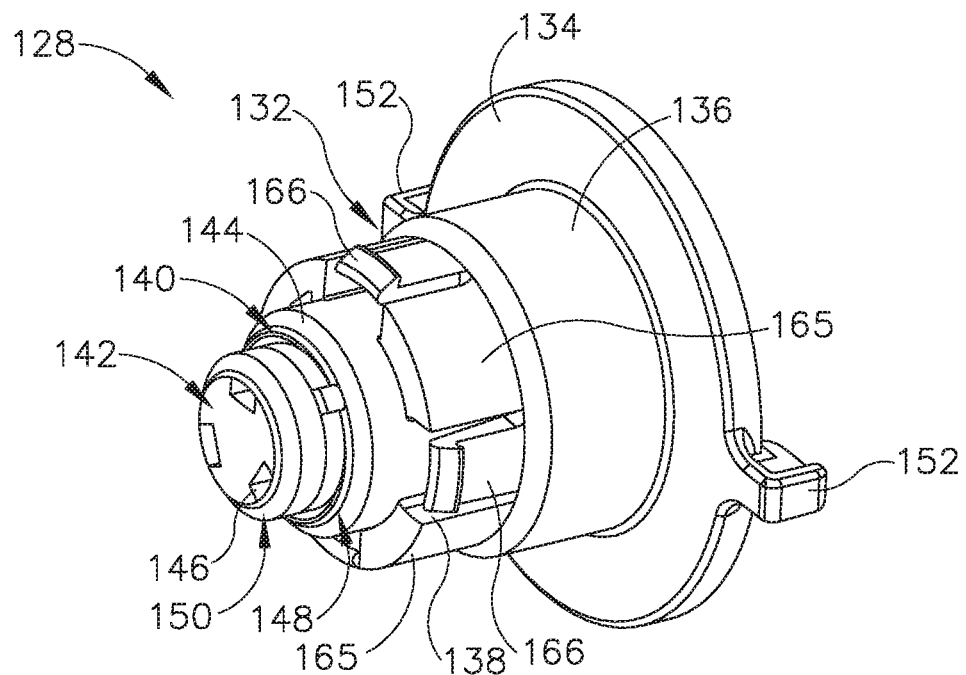
FIG. 5 depicts a front perspective view of a static coupling of the transducer slip joint of FIG. 4.
Figure 6:
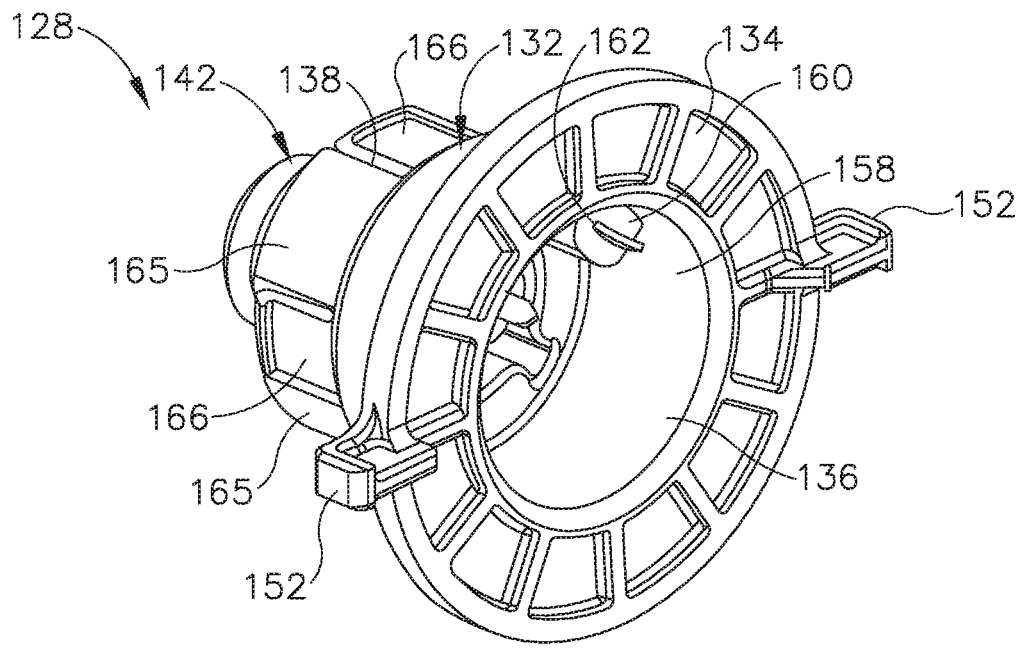
FIG. 6 depicts a rear perspective view of the static coupling of FIG. 5.
Figure 10:
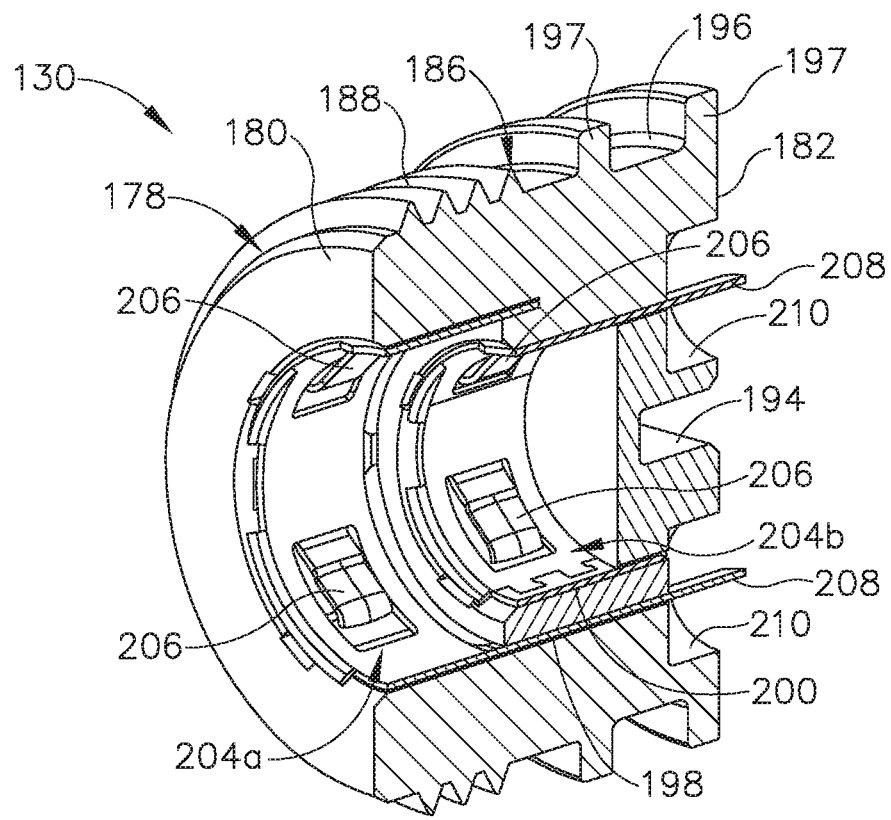
FIG. 10 depicts a rear sectional perspective view of the dynamic coupling of FIG. 8 taken along section line 10-10 of FIG. 9.
Figure 11:
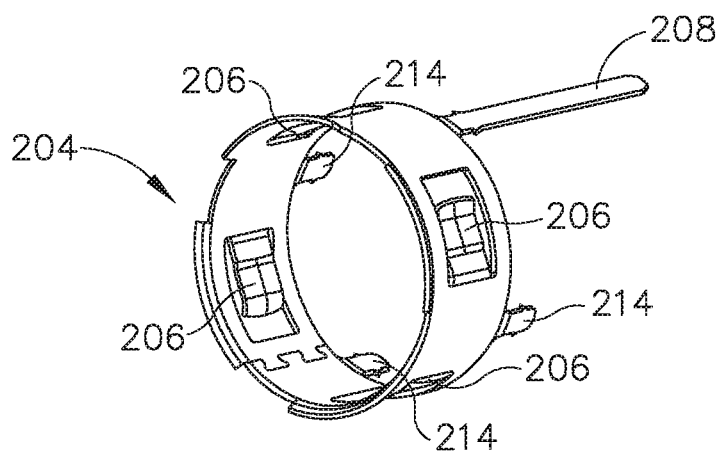
FIG. 11 depicts a rear perspective view of an electrical contact of the dynamic coupling of FIG. 8.

As shown in FIGS. 4-6, static coupling (128) includes a static body (132) having a series of annular portions narrowing in the distal direction along the longitudinal axis. The series of annular portions from the largest diameter proximal portion to the smallest diameter distal portion more particularly includes a proximal flange (134), an electrical potting well (136), a connection collar (138), an outer post (140), and an inner post (142). Static body (132) of the present example is integrally and unitarily formed of an electrically non-conductive material so as inhibit electrical power from inadvertently passing therethrough and shorting the electrical power supplied by wires (126). Of course, it will be appreciated that static body (132) may be alternatively formed of various components assembled together using known fasteners and/or other mechanically coupled structures.

While static body (132) is electrically non-conductive, static coupling (128) further includes electrically conductive contacts, also referred to herein as outer and inner cable contacts (144, 146). Outer and inner cable contacts (144, 146), described below in additional detail, are respectively secured to outer and inner posts (140, 142) to respectively define outer and inner terminals (148, 150). Outer and inner terminals (148, 150) of the present example correspond to positive and negative terminals (148, 150) configured to electrically connect to positive and negative wires (126). Of course, alternative wiring for reversing the polarity of these terminals (148, 150) may be used as desired for properly coupling electrical power from cable (33) to transducer assembly (30) in other examples.

Static body (132) is configured to be inserted distally through proximal opening (122) of transducer housing (114) into proximal hollow (118) until proximal flange (134) abuts against transducer housing (114) to limit further insertion. Proximal flange (134) also includes a pair of opposing tabs (152) configured to engage body (18) to inhibit rotation of the static body (132) relative to body (18). Each housing (56) includes a pair of longitudinally extending interior ribs (154) defining a longitudinal slot (156) therebetween. Each longitudinal slot (156) receives the respective tab (152) extending from proximal flange (134) such that static body (132) may longitudinally slide for insertion and/or removal within longitudinal slot (156), while ribs (154) rotatably engage with tabs (152) to thereby inhibit rotation of static body (132) relative to housings (56).

As shown in FIGS. 4-6, electrical potting well (136) extends distally from proximal flange (134) and defines an inner bore (158) in which to mechanically mount wires (126) for electrical connection with outer and inner cable contacts (144, 146). A pair of contact bases (160) extend longitudinally within electrical potting well (136) about inner bore (158) and are configured to receive proximal contact members (162) of outer and inner cable contacts (144, 146), as described below in greater detail. Electrical potting well (136) thereby provides space for mechanically mounting wires (126), and it will be appreciated that any know structure for mounting wires (126) within electrical potting well (136), such as directly to proximal contact members (162), may be used in accordance with the invention.

An outer surface of electrical potting well (136) is further configured to receive an annular dynamic seal (163) for inhibiting foreign matter, such as debris and/or fluid, from passing distally beyond annular dynamic seal (163) and further into proximal hollow (118). The proximal end of transducer housing (114) includes an annular proximal groove (164) configured to receive annular dynamic seal (163) that surrounds proximal opening (122) and is concentrically aligned along the longitudinal axis. Annular dynamic seal (163) is thereby positioned between the outer surface of electrical potting well (136) and the inner surface of transducer housing (114). In addition, annular dynamic seal (163) is configured to provide for relative rotation between transducer housing (114) and static coupling (128) while still inhibiting the distal passage of foreign matter toward transducer (112). As will be described below, additional seals may be used in accordance with the invention herein for inhibiting foreign matter from being introduced into various parts of slip joint (110) and transducer assembly (30). Of course, alternative examples may use more seals or even no seals so long as slip joint (110) and transducer assembly (30) are operational in view of a desirable use. The invention is thus not intended to be unnecessarily limited to the seal arrangements described herein.

Connection collar (138) extends distally from electrical potting well (136) and includes a plurality of longitudinally extending support guides (165) and a plurality of longitudinally extending snaps (166). Support guides (165) and snaps (166) are angularly positioned about connection collar (138) and alternate with one snap (166) between a pair of support guides (165) and vice versa. Exemplary connection collar (138) includes four support guides (165) and four snaps (166). Each snap (166) resiliently extends from electrical potting well (136) and is configured to deflect radially inward upon initial insertion into transducer housing (114), which includes an interior annular lip (168). As proximal flange (134) approaches transducer housing (114) during insertion of static body (132), resilient snaps (166) bias radially outward and engage interior annular lip (168) to limit proximal translation of static body (132) relative to transducer housing (114). Thus, snaps (166) and proximal flange (134) of static coupling (128) cooperate respectively with interior annular lip (168) and a proximal end of transducer housing (114) to longitudinally fix static coupling (128) to transducer housing (114). While the present example includes snaps (166) for longitudinally engaging transducer housing (114), it will be appreciated that alternative fasteners may be used for such securement, and the invention described herein is not intended to be unnecessarily limited to snaps (166).

While static coupling (128) is longitudinally fixed relative to transducer housing (114), transducer housing (114) and static coupling (128) remain configured for relative rotation. More particularly, snaps (166) longitudinally overlap with interior annular lip (168) to limit longitudinal movement, but snaps (116) provide little to no rotational engagement with transducer housing (114). Even in the event of some frictional engagement between connection collar (138) and transducer housing (114), transducer housing (114) is still configured to rotate relative to static coupling (128). In some examples, slip joint (110) may further include various coatings on one or more surfaces prone to relative rotation therebetween to reduce friction during use. In any case, transducer housing (114) is generally configured to freely rotate on connection collar (138) as desired.

Outer post (140) is rigidly connected to connection collar (138) radially inward from support guides (165) and extends distally therefrom. Similarly, inner post is rigidly connected to outer post (140) radially inward therefrom and extends distally toward dynamic coupling (130). Each outer and inner post (140, 142) is generally cylindrical with respective distal annular surfaces (not shown). Each of the distal annular surfaces (not shown) respectively receives outer and inner cable contacts (144, 146) as shown in FIGS. 5-7. More particularly, outer and inner cable contacts (144, 146) have respective distal annular rings (174) that circumscribe distal annular surfaces (not shown) for providing electrical connection regardless of the rotational position of dynamic coupling (130) relative to static coupling (128). Proximal contact members (162) extend proximally from distal annular rings (174) into electrical potting well (136) for connection with wires (126) as discussed above. In addition, a plurality of anchor members (176) also proximally extend from distal annular ring (174) and are configured to secure outer and inner cable contacts (144, 146) to outer and inner posts (140, 142) to form outer and inner terminals (148, 150). In one example, distal annular ring (174), anchor members (176), and proximal contact member (162) are unitarily and integrally formed together from an electrically conductive material and may be gold plated for additional conductivity. However, it will be appreciated that alternative construction of various components for forming outer and inner cable contacts (144, 146) may also be used with other examples. The invention described herein is thus not intended to be unnecessarily limited to the unitarily and integrally formed outer and inner cable contacts (144, 146) shown in the present example.

FIGS. 4 and 8-11 show first exemplary dynamic coupling (130) in greater detail. To this end, dynamic coupling (130) includes a dynamic body (178) with a generally cylindrical shape. Dynamic body (178) includes a proximal face (180) configured to receive static coupling (128), a distal face (182) configured to abut against transducer (112), and an outer annular surface (186) configured to secure within transducer housing (114). Outer annular surface (186) of the present example includes a plurality of outer threads (188) that threadably engage a plurality of inner threads (190) circumscribing distal hollow (120). During installation within distal hollow (120), dynamic coupling (130) is rotatably driven proximally until proximal face (180) of dynamic body (178) engages a seat (192) within distal hollow (120) of transducer housing (114). Distal face (182) of the present example further includes a linear slot (194) for further tool grip during installation. In addition, a static seal (195) surrounds a portion of outer annular surface (186) within an annular groove (196) between a pair of outer annular flanges (197). An inner surface of dynamic body (178) thus compresses against static seal (195) for further sealing transducer (112) and inhibiting distal transmission of foreign matter across static seal (195) that may have passed by dynamic seal (163) (see FIG. 4).

Dynamic body (178) further includes an outer bore (198) and an inner bore (200). Outer bore (198) has a larger diameter than inner bore (200), but is generally shallower than inner bore (200). Outer and inner bores (198, 200) are concentrically aligned along the longitudinal axis and positioned to respectively receive outer and inner terminals (148, 150) of static coupling (128). In addition, outer and inner bore (198, 200) have respective annular transducer contacts (204a, 204b) mounted therein. Each transducer contact (204a, 204b) includes a plurality of resilient and inwardly extending contact arms (206) angularly positioned about outer and inner bores (198, 200) to extend toward and contact outer and inner cable contacts (144, 146) of static coupling (128) for electrical communication therebetween. While the exemplary transducer contacts (204a, 204b) each have four contact arms (206) equiangularly positioned about outer and inner bores (198, 200), it will be appreciated that alternative numbers and positioning for transducer contacts (204a, 204b) may be placed as desired for maintaining electrical communication with outer and inner cable contacts (144, 146).

Each transducer contact (204a, 204b) further includes a distal contact member (208) that distally extends through proximal face (180) to distal face (182). Specifically, each distal contact member (208) distally terminates within a distal potting well (210) on distal face (182). Each distal potting well (210) is configured to provide sufficient space in which to electrically connect transducer (112) to transducer contacts (204a, 204b), such as by additional wires (212). Each transducer contact (204a, 204b) also has a pair of opposing anchor members (214) to rigidly secure each transducer contact (204a, 204b) respectively within each outer and inner bore (198, 200).

As shown and described herein with respect to the present example, transducer contacts (204a, 204b) define an outer profile about the longitudinal axis in a plane that is transverse to the longitudinal axis, and outer and inner cable contacts (144, 146) each respectively define outer profiles about the longitudinal axis in a plane that is transverse to the longitudinal axis. The outer profiles for each transducer contact (204a, 204b) and outer and inner cable contacts (144, 146) are smaller than the outer profile of transducer (34) with piezoelectric elements (36) as well as transducer housing (114). In addition, the outer and inner cable contacts (144, 146) are also smaller than the respective outer profiles of transducer contacts (204a, 204b). Accordingly, the outer profiles of outer and inner cable contacts (144, 146) and transducer contacts (204a, 204b) are all nested within the outer profiles of transducer (34) and transducer housing (114) for reducing the size of transducer assembly (30) and slip joint (110). The overall size of body (18) for containing transducer assembly (30) and slip joint (110) is thus reduced about the longitudinal axis as compared to alternative slip joints that surround transducer assembly (30) for smaller, more convenient containment that may be more easily manipulated by the user.

In use, FIGS. 3-11 show transducer assembly (30) mechanically and electrically coupled with cable (33) via slip joint (110). During manipulation of surgical instrument (10) and treatment of a patient, the user selectively rotates knob (54) for positioning end effector (16) at a desirable angular orientation about the longitudinal axis of shaft assembly (14). In doing so, the user also collectively rotates shaft assembly (14), waveguide (38), and transducer assembly (30) about the longitudinal axis of shaft assembly (14). Dynamic coupling (130), which is electrically and mechanically coupled with transducer (112), also rotates with transducer assembly (30), whereas static coupling (128) remains rotationally fixed relative to instrument body (18). More particularly, interior ribs (154) engage tabs (152) to inhibit rotation of static coupling (128) while longitudinally fixed within distal portion (116) of transducer housing (114) through proximal opening (122).

In order to maintain electrical communication between static and dynamic couplings (128, 130), contact arms (206) of transducer contacts (204a, 204b) remain radially biased against outer and inner cable contacts (144, 146) as contact arms (206) rotate about outer and inner cable contacts (144, 146). The user may thus move transducer assembly (30) to any rotational position about the longitudinal axis and contact arms (206) will remain in physical contact with outer and inner cable contacts (144, 146) to maintain electrical communication between transducer (112) and cable (33).

While dynamic coupling (130) rotates, static coupling (128) remains stationary relative to instrument body (18). Cable (33) with wires (126) connected to static coupling (138) is thus inhibited from rotating relative to instrument body (18) in order to further inhibit cable (33) from winding during rotation of transducer assembly (30).

B. Second Exemplary Slip Joint

FIGS. 12-15 show a second exemplary slip joint (310) connected with transducer assembly (30). Transducer assembly (30) has transducer (112) contained within a transducer housing (314). Slip joint (310) is integrated into a distal portion (316) of transducer housing (314) having a proximal hollow (318) and an adjacent distal hollow (320). Proximal hollow (318) extends between distal hollow (320) and a proximal opening (322) to the exterior of transducer housing (314) within body (18). In the present example, slip joint (310) is positioned generally within distal hollow (320) and proximal hollow (322) along the longitudinal axis. More particularly, slip joint (310), distal hollow (320), and proximal hollow (322) are concentrically aligned along the longitudinal axis, and distal hollow (320) has a larger diameter than proximal hollow (322).

Transducer housing (314) defines an outer profile about the longitudinal axis in a plane that is transverse to the longitudinal axis. Slip joint (310) is integrated into distal portion (316) of transducer housing (314) such that slip joint (310) is transversely sized to fit within the outer profile of transducer housing (314). In the present example, an outer profile in the transverse plane of slip joint (310) is smaller than the outer profile of transducer housing (314) about the longitudinal axis. In addition, transducer (34) with piezoelectric elements (36) also defines an outer profile in the transverse plane that is smaller than the outer profile of transducer housing (314). By way of further example, the outer profile of the transducer (34) with piezoelectric elements (36) is larger than the outer profile of slip joint (310).

Similar to slip joint (110) (see FIG. 4), slip joint (310) also includes a proximal static coupling (328) positioned in proximal hollow (318) and a distal dynamic coupling (330) positioned within distal hollow (320). Static coupling (328) receives electrical power from positive and negative wires (126) and directs electrical power to dynamic coupling (330) for powering transducer assembly (30). Transducer housing (314) in turn mechanically supports static and dynamic couplings (328, 330) against each other to transmit the electrical power therebetween while providing for relative motion between static and dynamic couplings (328, 330).

Figure 12:
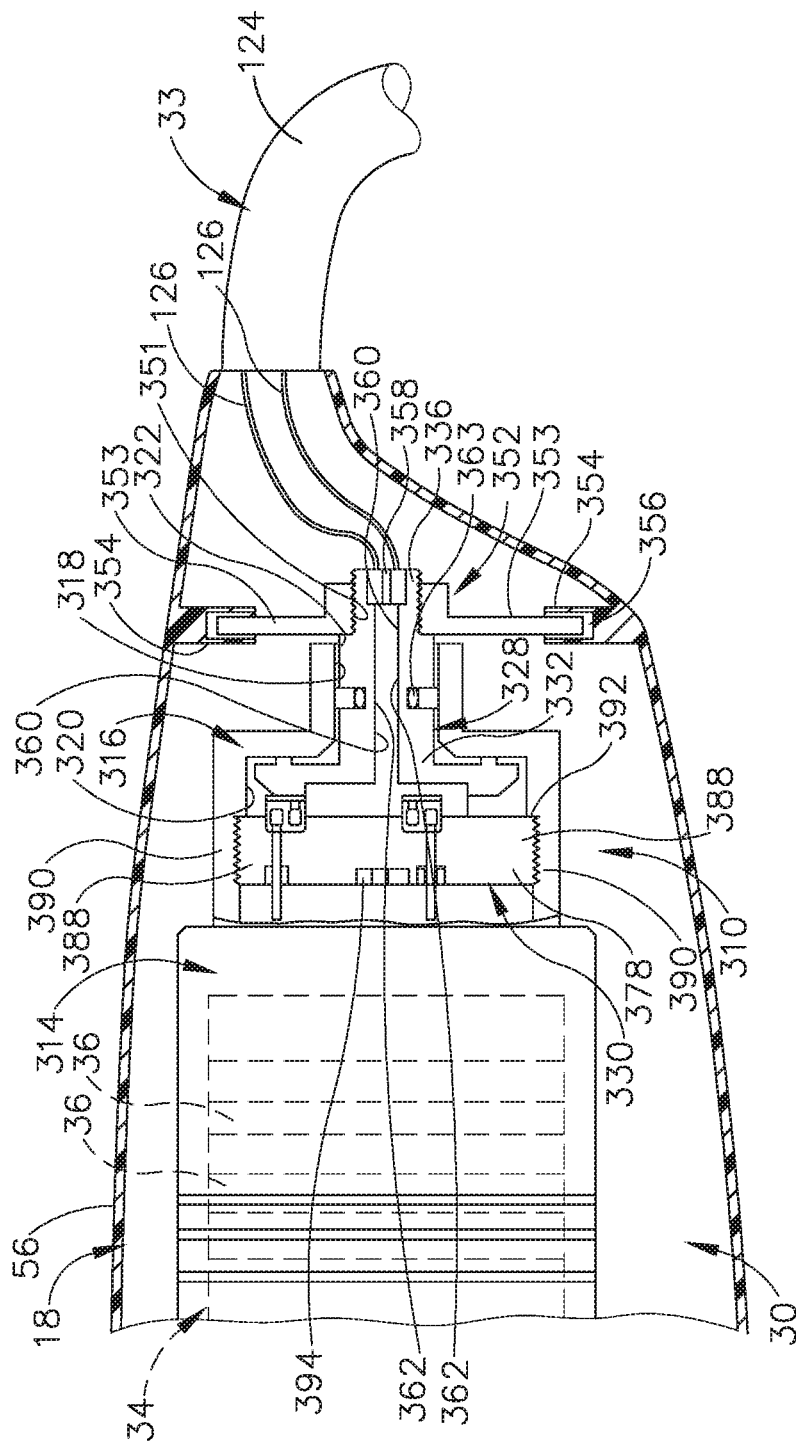
FIG. 12 depicts an enlarged cross-sectional view of a handle assembly of another ultrasonic surgical instrument, with a second exemplary transducer slip joint.
Figure 13:
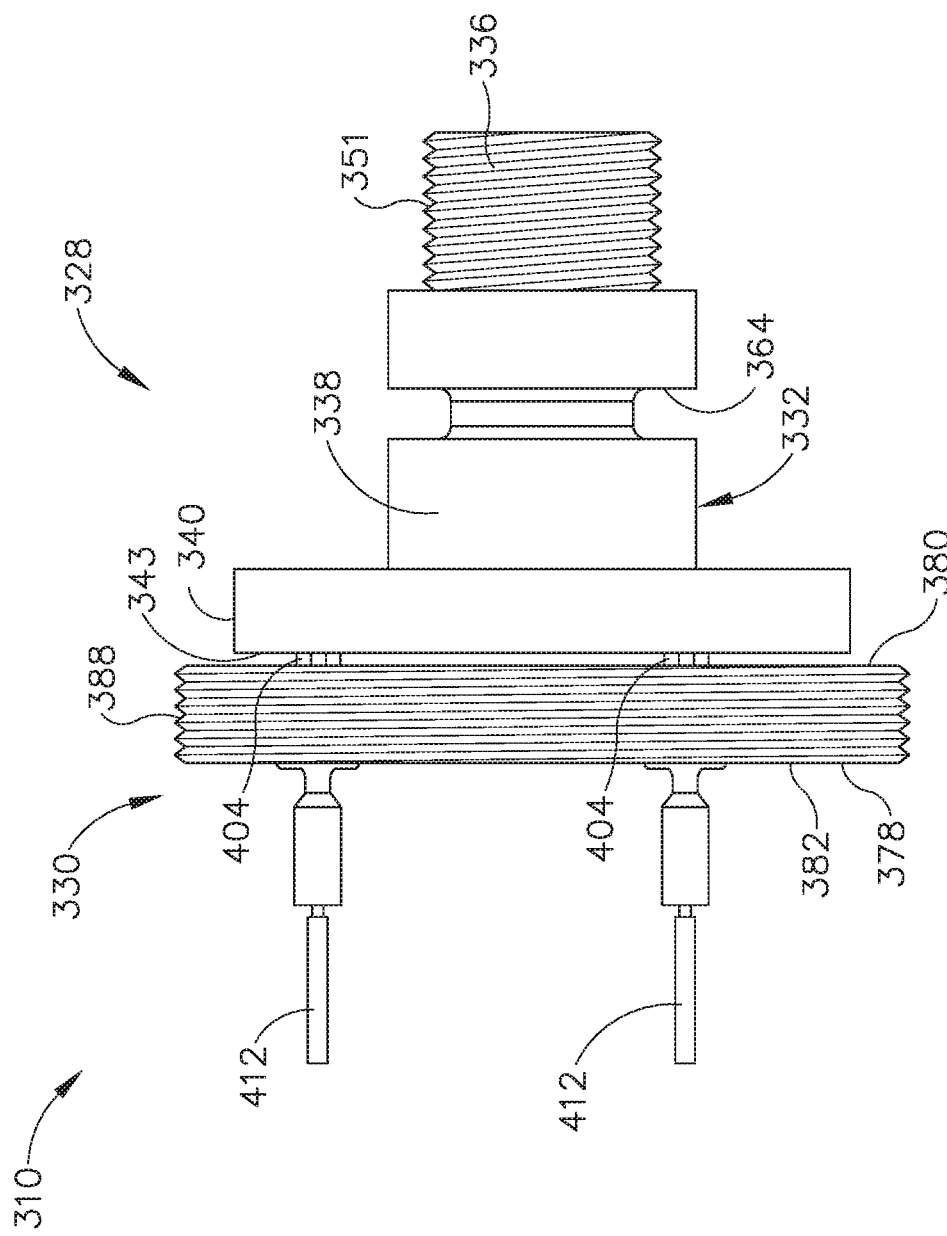
FIG. 13 depicts a side elevational view of the transducer slip joint of FIG. 12.
Figure 14:
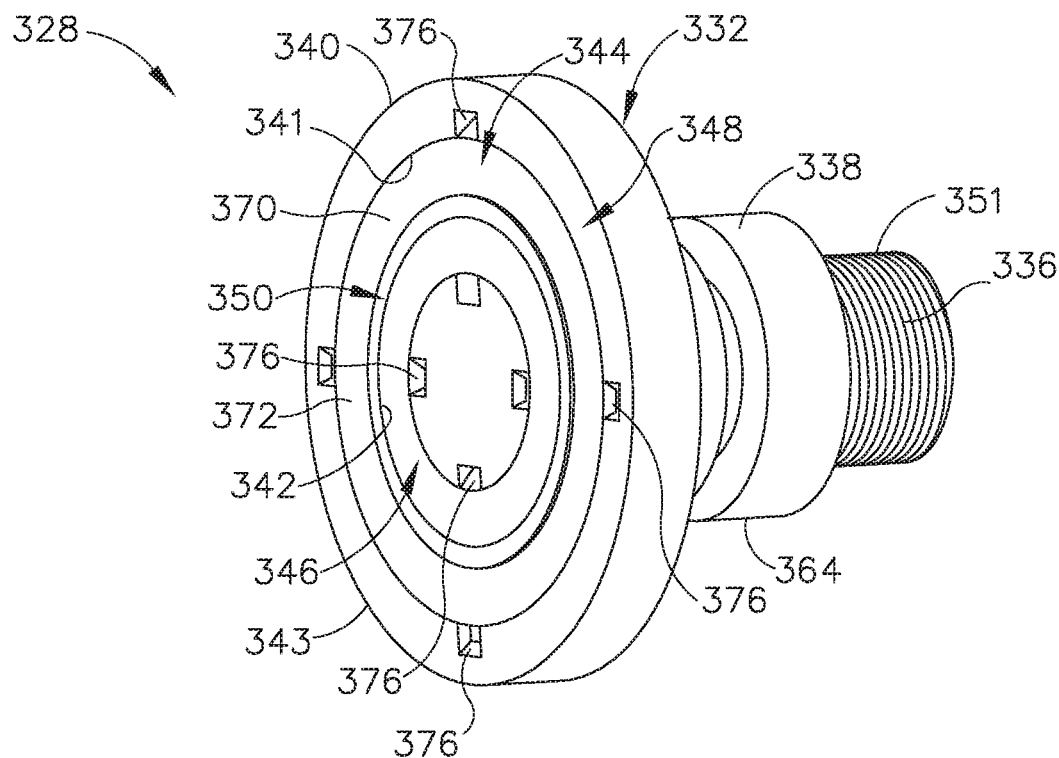
FIG. 14 depicts a front perspective view of a static coupling of the transducer slip joint of FIG. 12.

As shown in FIGS. 12-14, static coupling (328) includes a static body (332) having a series of annular portions narrowing in the proximal direction along the longitudinal axis. The series of annular portions from the smallest diameter proximal portion to the largest diameter distal portion more particularly includes an electrical potting well (336), a cylindrical neck (338), and a distal cylindrical wall (340). Static body (332) of the present example is integrally and unitarily formed of an electrically non-conductive material so as inhibit electrical power from inadvertently passing therethrough and shorting the electrical power supplied by wires (126). Of course, it will be appreciated that static body (332) may be alternatively formed of various components assembled together using known fasteners and/or other mechanically coupled structures.

While static body (332) is electrically non-conductive, static coupling (128) further includes outer and inner cable contacts (344, 346). Outer and inner cable contacts (344, 346), described below in additional detail, are respectively secured within outer and inner annular grooves (341, 342) on a distal face (343) to respectively define outer and inner terminals (348, 350). Outer and inner terminals (348, 350) of the present example correspond to positive and negative terminals (348, 350) configured to electrically connect to positive and negative wires (126). Of course, alternative wiring for reversing the polarity of these terminals (348, 350) may be used as desired for properly coupling electrical power from cable (34) to transducer assembly (30) in other examples.

Static body (332) is configured to be inserted proximally through proximal opening (122) of transducer housing (114) by way of distal and proximal hollows (320, 318) until distal cylindrical wall (340) abuts against transducer housing (314) within distal hollow (320) to limit further insertion. Specifically, electrical potting well (336) projects through proximal opening (322) and proximally from transducer housing (314). An outer surface of electrical potting well (336) includes a plurality of threads (352) configured to threadably receive a fastener, such as a wingnut (353) having a pair of opposing tabs (353) configured to engage body (18) for inhibiting rotation of wingnut (353) and static body (332) relative to body (18). Body (18) includes a pair of upper and lower interior ribs (354) defining a transverse slot (356) therebetween. Each transverse slot (356) receives the respective tab (353) of wingnut (352), while ribs (354) rotatably engage with tabs (353) to thereby inhibit rotation of static body (332) relative to body (18).

Electrical potting well (336) defines an inner bore (358) in which to mechanically mount wires (126) for electrical connection with outer and inner cable contacts (344, 346). A pair of contact channels (360) extend longitudinally from distal face (343) through neck (338) and to electrical potting well (336) and are configured to receive proximal contact members (362) of outer and inner cable contacts (344, 346), as described below in greater detail. Electrical potting well (336) thereby provides space for mechanically mounting wires (126), and it will be appreciated that any know structure for mounting wires (126) within electrical potting well (336), such as directly to proximal contact members (362), may be used in accordance with the invention.

Neck (338) extends distally from electrical potting well (36) to distal cylindrical wall (340) for a rigid connection therebetween through proximal hollow (318). Neck (338) is further configured to receive an annular dynamic seal (363) for inhibiting foreign matter, such as debris and/or fluid, from passing distally beyond annular dynamic seal (363) and further into proximal hollow (318). Neck (338) includes an annular proximal groove (364) configured to receive annular dynamic seal (363) that circumscribes proximal hollow (318) against an inner surface of transducer housing (314). In the present example, annular dynamic seal (363) is concentrically aligned along the longitudinal axis positioned between the outer surface of neck (338) and the inner surface of transducer housing (314). In addition, annular dynamic seal (363) is configured to provide for relative rotation between transducer housing (314) and static coupling (328) while still inhibiting the distal passage of foreign matter fluid toward transducer (112).

With distal cylindrical wall (340) positioned distally adjacent to proximal hollow (320), wingnut (352) positioned proximally adjacent to proximal hollow (320), and neck (338) extending therebetween, static coupling (328) is longitudinally fixed relative to transducer housing (314), but still configured for relative rotation. To aid with relative rotation, engagement surfaces prone to generate friction between static coupling (328) and transducer housing (314) may be coated in with a low-friction coating, such as silicon. Still, even in the event of some frictional engagement between static coupling (328) and transducer housing (314), transducer housing (314) is still configured to rotate relative to static coupling (328).

Distal cylindrical wall (340) distally extends from neck (338) to a distal face (343) that includes outer and inner terminals (348, 350). More particularly, outer and inner cable contacts (344, 346) respectively include outer and inner annular rings (370, 372) having proximal contact members (362) extending proximally into electrical potting well (336) for connection with wires (126) as discussed above. In the present example, outer annular ring (370) has a larger diameter than inner annular ring (372) and inner annular ring (372) is positioned concentrically within outer annular ring (370). In addition, a plurality of anchor members (376) also proximally extend from outer and inner annular rings (370, 372) and are configured to secure outer and inner cable contacts (344, 346) distal face (343) within outer and inner annular grooves (341, 342) to form outer and inner terminals (348, 350). In some versions, each of the outer and inner cable contacts (344, 346) are unitarily and integrally formed from an electrically conductive material and may be gold plated for additional conductivity. However, it will be appreciated that alternative construction of various components for forming outer and inner cable contacts (344, 346) may also be used with other examples. The invention described herein is thus not intended to be unnecessarily limited to the unitarily and integrally formed outer and inner cable contacts (344, 346) shown in the present example.

Figure 15:
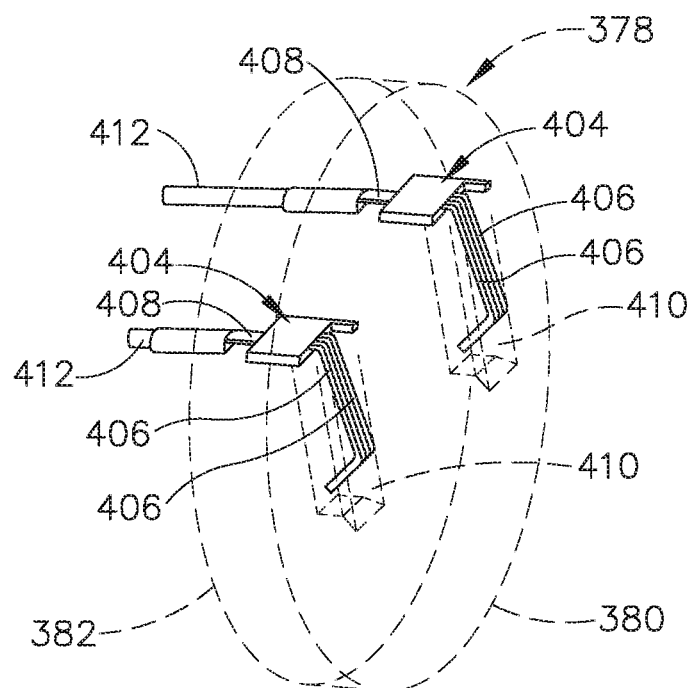
FIG. 15 depicts a rear perspective view of a dynamic coupling of the transducer slip joint of FIG. 12.

FIGS. 12, 13, and 15 show first exemplary dynamic coupling (330) in greater detail. To this end, dynamic coupling (330) includes a dynamic body (378) with a generally cylindrical shape. Dynamic body (378) includes a proximal face (380) configured to receive static coupling (328), a distal face (382) configured to abut against transducer (112), and an outer annular surface (386) configured to secure within transducer housing (314). Outer annular surface (386) of the present example includes a plurality of outer threads (388) that threadably engage a plurality of inner threads (390) circumscribing distal hollow (320). During installation within distal hollow (320), dynamic coupling (330) is rotatably driven proximally until proximal face (380) of dynamic body (378) engages a seat (392) within distal hollow (320) of transducer housing (314). Distal face (182) of the present example further includes mechanically engageable recess (394), such as a hex recess, for tool grip during installation.

Dynamic body (178) further includes an outer bore (398) positioned radially outward from an inner bore (400). Outer bore (398) radially aligns with outer cable contact (344) about the longitudinal axis, whereas inner bore (400) radially aligns with inner cable contact (346) about the longitudinal axis. Each outer and inner bore (398, 400) receives a transducer contact (404) with a plurality of resilient and proximally extending contact arms (406). Contact arms (406) are thereby positioned to extend proximally and contact outer and inner cable contacts (344, 346) of static coupling (328) for electrical communication therebetween.

Each transducer contact (404) further includes a distal contact member (408) that distally extends from arms (406) from proximal face (380) to distal face (382). Specifically, each distal contact member (308) distally terminates within a distal potting well (410) on distal face (482). Each distal potting well (410) is configured to provide sufficient space in which to electrically connect transducer (412) to transducer contacts (404), such as by additional wires (412). Each transducer contact (404) also has a pair of opposing anchor members (not shown) to rigidly secure each transducer contact (404) within its respective outer and inner bore (398, 400).

As shown and described herein with respect to the present example, transducer contacts (404) define an outer profile about the longitudinal axis in a plane that is transverse to the longitudinal axis, and outer and inner cable contacts (344, 346) each respectively define outer profiles about the longitudinal axis in a plane that is transverse to the longitudinal axis. The outer profiles for each transducer contact (404) and outer and inner cable contacts (344, 346) are smaller than the outer profile of transducer (34) with piezoelectric elements (36) as well as transducer housing (414). Accordingly, the outer profiles of outer and inner cable contacts (344, 346) and transducer contacts (404) are all nested within the outer profiles of transducer (34) and transducer housing (314) for reducing the size of transducer assembly (30) and slip joint (310). The overall size of body (18) for containing transducer assembly (30) and slip joint (310) is thus reduced about the longitudinal axis as compared to alternative slip joints that surround transducer assembly (30) for smaller, more convenient containment that may be more easily manipulated by the user.

In use, FIGS. 12-15 show transducer assembly (30) mechanically and electrically coupled with cable (33) via slip joint (310). During manipulation of surgical instrument (10) and treatment of a patient, the user selectively rotates knob (54) for positioning end effector (16) at a desirable angular orientation about the longitudinal axis of shaft assembly (14). In doing so, the user also collectively rotates shaft assembly (14), waveguide (38), and transducer assembly (30) about the longitudinal axis of shaft assembly (14). Dynamic coupling (330), which is electrically and mechanically coupled with transducer (112), also rotates with transducer assembly (30), whereas static coupling (328) remains rotationally fixed relative to instrument body (18). More particularly, upper and lower interior ribs (354) engage tabs (352) to inhibit rotation of static coupling (328) while longitudinally fixed within distal portion (316) of transducer housing (314) through proximal opening (322).

In order to maintain electrical communication between static and dynamic couplings (328, 330), contact arms (406) of outer and inner transducer contacts (404) remain proximally biased against outer and inner cable contacts (344, 346) as contact arms (406) rotate about outer and inner cable contacts (344, 346). The user may thus move transducer assembly (30) to any rotational position about the longitudinal axis and contact arms (406) will remain in physical contact with outer and inner cable contacts (344, 346) to maintain electrical communication between transducer (112) and cable (33).

While dynamic coupling (330) rotates, static coupling (328) remains stationary relative to instrument body (18). Cable (33) with wires (126) connected to static coupling (338) is thus inhibited from rotating relative to instrument body (18) in order to further inhibit cable (33) from winding during rotation of transducer assembly (30).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) an instrument body; (b) an ultrasonic transducer assembly rotatably mounted along a longitudinal axis within the instrument body such that the ultrasonic transducer assembly is configured to selectively rotate about the longitudinal axis, wherein the ultrasonic transducer assembly defines a first outer profile that is transverse to the longitudinal axis; (c) a power cord projecting from the instrument body and configured to provide electrical power to the ultrasonic transducer assembly for operating an acoustic waveguide; and (d) a transducer slip joint positioned between the power cord and the ultrasonic transducer assembly and defining a second outer profile that is transverse to the longitudinal axis, wherein the transducer slip joint is configured to electrically connect the power cord to the ultrasonic transducer assembly and mechanically connect the power cord to the ultrasonic transducer assembly such that the ultrasonic transducer assembly is configured to selectively rotate relative to the power cord for inhibiting the power cord from winding upon rotation of the ultrasonic transducer assembly relative to the instrument body, wherein the second outer profile fits within the first outer profile of the ultrasonic transducer assembly.

Example 2

The surgical instrument of Example 1, wherein the transducer slip joint includes: (i) a proximal coupling affixed to the power cord and having a first electrical cord contact and a second electrical cord contact, wherein each of the first and second electrical cord contacts are electrically connected to the power cord, wherein at least one of the first and second electrical cord contacts provides at least one distally oriented electrical contact, and (ii) a distal coupling affixed to the ultrasonic transducer assembly and having a first electrical transducer contact and a second electrical transducer contact, wherein each of the first and second electrical transducer contacts is electrically connected to the ultrasonic transducer assembly, wherein at least one of the first and second electrical transducer contacts provides at least one proximally oriented electrical contact, wherein the at least one distally oriented electrical contact is configured to slidingly engage the at least one proximally oriented electrical contact, wherein the proximal and distal couplings are secured together such that the distal coupling is configured to rotate with the ultrasonic transducer assembly relative to the proximal coupling while maintaining electrical connections between the first electrical cord contact and the first electrical transducer contact as well as the second electrical cord contact and the second electrical transducer contact.

Example 3

The surgical instrument of Example 2, wherein the proximal and distal couplings are positioned axially along the longitudinal axis such that the distal coupling is configured to rotate relative to the proximal coupling about the longitudinal axis.

Example 4

The surgical instrument of Example 3, wherein the proximal and distal couplings are further secured together such that the proximal coupling is longitudinally fixed to the distal coupling along the longitudinal axis.

Example 5

The surgical instrument of Example 4, wherein the proximal coupling is engaged with the instrument body to inhibit the proximal coupling from rotating within the instrument body.

Example 6

The surgical instrument of Example 5, wherein the instrument body includes an interior rib and the proximal coupling further includes a proximal body and a tab extending radially outwardly from the proximal body, wherein the interior rib is configured to receive the tab thereagainst such that the interior rib inhibits the proximal coupling from rotating within the instrument body.

Example 7

The surgical instrument of any one or more of Examples 5 through 6, wherein the instrument body includes an interior rib and the proximal coupling further includes a proximal body and a wingnut threaded thereon, wherein the interior rib is configured to receive the wingnut thereagainst such that the interior rib inhibits the proximal coupling from rotating within the instrument body.

Example 8

The surgical instrument of any one or more of Examples 2 through 7, wherein the ultrasonic transducer assembly includes a transducer housing extending along the longitudinal axis, wherein the transducer housing has a distal end portion with a distal hollow and an adjacent proximal hollow, wherein the distal coupling is secured against the transducer housing within the distal hollow such that the transducer housing inhibits rotation and translation relative to the transducer housing, wherein the proximal coupling is secured against the transducer housing within the proximal hollow such that the transducer housing inhibits translation relative to the transducer housing and the proximal coupling is configured to rotate within the transducer housing.

Example 9

The surgical instrument of Example 8, wherein the transducer housing is configured to distally receive the proximal coupling within the proximal hollow, and wherein the proximal coupling includes a connection feature configured to longitudinally secure the proximal coupling within the transducer housing.

Example 10

The surgical instrument of Example 9, wherein the instrument body includes an interior rib and the proximal coupling further includes a proximal body and a tab extending radially outward from the proximal body, wherein the interior rib is configured to receive the tab thereagainst such that the interior rib inhibits the proximal coupling from rotating within the instrument body.

Example 11

The surgical instrument of any one or more of Examples 8 through 10, wherein the transducer housing has a proximal wall and is configured to proximally receive the proximal coupling through the distal hollow to within the proximal hollow, and wherein the proximal coupling is captured between the distal coupling and the proximal wall to longitudinally secure the proximal coupling within the transducer housing.

Example 12

The surgical instrument of Example 11, wherein the instrument body includes an interior rib and the proximal coupling further includes a proximal body and a wingnut threaded thereon, wherein the interior rib is configured to receive the wingnut thereagainst such that the interior rib inhibits the proximal coupling from rotating within the instrument body.

Example 13

The surgical instrument of any one or more of Examples 8 through 12, further comprising an annular dynamic seal positioned within the proximal hollow between the transducer housing and the proximal coupling received therein, wherein the annular dynamic seal is configured to inhibit foreign matter from being introduced further distally into the ultrasonic transducer assembly as the ultrasonic transducer assembly rotates about the proximal coupling.

Example 14

The surgical instrument of any one or more of Examples 2 through 13, wherein each of the first and second electrical cord contacts is annular.

Example 15

The surgical instrument of any one or more of Examples 1 through 14, further comprising: (a) a handle assembly including the instrument body and the ultrasonic transducer assembly; (b) a shaft assembly extending distally from the handle assembly; (c) an end effector extending distally from the shaft assembly; and (d) an acoustic waveguide operatively connected to the ultrasonic transducer assembly and extending distally therefrom along the shaft assembly to the end effector.

Example 16

A surgical instrument, comprising: (a) an instrument body; (b) an ultrasonic transducer assembly rotatably mounted along a longitudinal axis within the instrument body such that the ultrasonic transducer assembly is configured to selectively rotate about the longitudinal axis, wherein the ultrasonic transducer assembly; (c) a power cord projecting from the instrument body and configured to provide electrical power to the ultrasonic transducer assembly for operating an acoustic waveguide; and (d) a transducer slip joint positioned between the power cord and the ultrasonic transducer assembly, including: (i) a proximal coupling affixed to the power cord and having a first electrical cord contact electrically connected to the power cord, and (ii) a distal coupling affixed to the ultrasonic transducer assembly and having a first electrical transducer contact electrically connected to the ultrasonic transducer assembly, wherein the first electrical transducer contact is positioned radially outward from the first electrical cord contact relative to the longitudinal axis and slidingly receives the first electrical cord contact radially thereagainst such that the first electrical transducer contact and the first electrical cord contact are configured to communicate electrical power therebetween, wherein the transducer slip joint is configured to mechanically connect the power cord to the ultrasonic transducer assembly such that the ultrasonic transducer assembly is configured to selectively rotate relative to the power cord for inhibiting the power cord from winding upon rotation of the ultrasonic transducer assembly relative to the instrument body.

Example 17

The surgical instrument of Example 16, wherein the ultrasonic transducer assembly includes a transducer housing extending along the longitudinal axis, wherein the transducer housing has a distal end portion with a distal hollow and an adjacent proximal hollow, wherein the transducer housing is configured to distally receive the proximal coupling within the proximal hollow, and wherein the proximal coupling includes a connection feature configured to longitudinally secure the proximal coupling within the transducer housing.

Example 18

The surgical instrument of Example 17, wherein the proximal coupling has a second electrical cord contact electrically connected to the power cord, wherein the distal coupling has a second electrical transducer contact electrically connected to the ultrasonic transducer assembly, wherein the second electrical transducer contact is positioned radially outward from the second electrical cord contact relative to the longitudinal axis and slidingly receives the second electrical cord contact radially thereagainst such that the second electrical transducer contact and the second electrical cord contact are configured to communicate electrical power therebetween.

Example 19

A surgical instrument, comprising: (a) an instrument body; (b) an ultrasonic transducer assembly rotatably mounted along a longitudinal axis within the instrument body such that the ultrasonic transducer assembly is configured to selectively rotate about the longitudinal axis, wherein the ultrasonic transducer assembly; (c) a power cord projecting from the instrument body and configured to provide electrical power to the ultrasonic transducer assembly for operating an acoustic waveguide; and (d) a transducer slip joint positioned between the power cord and the ultrasonic transducer assembly, including: (i) a proximal coupling affixed to the power cord and having an electrical cord contact electrically connected to the power cord, and (ii) a distal coupling affixed to the ultrasonic transducer assembly and having an electrical transducer contact electrically connected to the ultrasonic transducer assembly, wherein the electrical transducer contact is positioned distally from the electrical cord contact relative and slidingly receives the electrical cord contact longitudinally thereagainst such that the electrical transducer contact and the electrical cord contact are configured to communicate electrical power therebetween, wherein the transducer slip joint is configured to mechanically connect the power cord to the ultrasonic transducer assembly such that the ultrasonic transducer assembly is configured to selectively rotate relative to the power cord for inhibiting the power cord from winding upon rotation of the ultrasonic transducer assembly relative to the instrument body.

Example 20

The surgical instrument of Example 19, wherein the ultrasonic transducer assembly includes a transducer housing extending along the longitudinal axis, wherein the transducer housing has a distal end portion with a distal hollow and an adjacent proximal hollow, wherein the transducer housing has a proximal wall and is configured to proximally receive the proximal coupling through the distal hollow to within the proximal hollow, and wherein the proximal coupling is captured between the distal coupling and the proximal wall to longitudinally secure the proximal coupling within the transducer housing.

IV. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Moreover, those of ordinary skill in the art will recognize that various teachings herein may be readily applied to electrosurgical instruments, stapling instruments, and other kinds of surgical instruments. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art.

For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) an ultrasonic transducer assembly configured to selectively rotate; and
   (b) a transducer slip joint configured to electrically connect a power cord with the ultrasonic transducer assembly, wherein the transducer slip joint comprises:
      (i) a first body rotatably coupled with the ultrasonic transducer assembly, and
      (ii) a second body rotatably coupled with the power cord, wherein the second body is at least partially longitudinally constrained relative to the first body.

2. The surgical instrument of claim 1, wherein the ultrasonic transducer assembly includes a plurality of piezoelectric elements, wherein the transducer slip joint is positioned proximal to the plurality of piezoelectric elements of the ultrasonic transducer assembly.

3. The surgical instrument of claim 1, wherein the ultrasonic transducer assembly defines a longitudinal axis, wherein the ultrasonic transducer assembly is configured to selectively rotate about the longitudinal axis.

4. The surgical instrument of claim 1, wherein the ultrasonic transducer assembly defines a longitudinal axis, wherein the transducer slip joint is configured to electrically connect a power cord with the ultrasonic transducer assembly such that the ultrasonic transducer assembly is configured to rotate about the longitudinal axis relative to the power cord while the power cord provides power to the ultrasonic transducer assembly.

5. The surgical instrument of claim 4, wherein one of the first or second bodies is configured to rotate relative to the other of the first and second bodies about the longitudinal axis.

6. The surgical instrument of claim 1, wherein one of the first or second bodies includes a resiliently biased contact arm configured to remain in contact with the other of the first or second bodies.

7. The surgical instrument of claim 6, wherein the second body comprises an annular contact member, wherein the first body includes the resiliently biased contact arm configured to abut against the annular contact member of the second body.

8. The surgical instrument of claim 7, wherein the resiliently biased contact arm is radially biased against the annular contact member.

9. The surgical instrument of claim 1, wherein the second body comprises a post extending along a longitudinal axis, wherein the first body is configured to rotate relative to the post.

10. The surgical instrument of claim 1, wherein the surgical instrument further comprises a housing, wherein the ultrasonic transducer assembly is rotatably mounted to the housing, wherein the second body is rotationally fixed about a longitudinal axis via the housing.

11. The surgical instrument of claim 1, further comprising the power cord configured to provide electrical power to the ultrasonic transducer assembly.

12. The surgical instrument of claim 1, further comprising:
   (a) a handle assembly that includes the ultrasonic transducer assembly;
   (b) a shaft assembly extending distally from the handle assembly;
   (c) an end effector extending distally from the shaft assembly; and
   (d) an acoustic waveguide operatively connected to the ultrasonic transducer assembly and extending distally therefrom along the shaft assembly to the end effector.

13. A surgical instrument, comprising:
   (a) an ultrasonic transducer assembly that defines a longitudinal axis, wherein the ultrasonic transducer assembly is configured to selectively rotate about the longitudinal axis, wherein the ultrasonic transducer assembly defines a first outer profile that is transverse to the longitudinal axis; and
   (b) a transducer slip joint configured to electrically connect a power cord with the ultrasonic transducer assembly, wherein the transducer slip joint defines a second outer profile that is transverse to the longitudinal axis, wherein the second outer profile fits within the first outer profile of the ultrasonic transducer assembly.

14. The surgical instrument of claim 13, wherein the transducer slip joint comprises:
   (i) a first body rotatably coupled with the ultrasonic transducer assembly, and
   (ii) a second body rotatably coupled with the power cord.

15. The surgical instrument of claim 14, wherein the second body is at least partially longitudinally constrained relative to the first body.

16. The surgical instrument of claim 14, wherein the second body is in direct contact with the ultrasonic transducer assembly.

17. The surgical instrument of claim 13, further comprising the power cord configured to provide electrical power to the ultrasonic transducer assembly.

18. The surgical instrument of claim 13, wherein the transducer slip joint is configured to electrically connect the power cord with the ultrasonic transducer assembly and mechanically connect the power cord to the ultrasonic transducer assembly.

19. A surgical instrument, comprising:
   (a) an ultrasonic transducer assembly configured to selectively rotate; and
   (b) a transducer slip joint configured to electrically connect a power cord with the ultrasonic transducer assembly, wherein the transducer slip joint comprises:
      (i) a first body rotatably coupled with the ultrasonic transducer assembly, and
      (ii) a second body rotatably coupled with the power cord, and
      (iii) a seal positioned between the first and second bodies and configured to inhibit a foreign matter from being introduced between the first and second bodies.

20. The surgical instrument of claim 19, wherein the ultrasonic transducer assembly defines a longitudinal axis, wherein the ultrasonic transducer assembly is configured to selectively rotate about the longitudinal axis.

* * * * *